US008592617B2

(12) United States Patent
Hill et al.

(10) Patent No.: US 8,592,617 B2
(45) Date of Patent: Nov. 26, 2013

(54) REDOX MEDIATORS

(75) Inventors: Hugh Oliver Allen Hill, Yarnton (GB);
Christopher Paul Newman, Yarnton (GB); Luet Lok Wong, Yarnton (GB);
Tai-Chu Lau, Hong Kong (CN)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1324 days.

(21) Appl. No.: 12/158,371

(22) PCT Filed: Dec. 21, 2006

(86) PCT No.: PCT/GB2006/004855
§ 371 (c)(1),
(2), (4) Date: Sep. 25, 2008

(87) PCT Pub. No.: WO2007/072018
PCT Pub. Date: Jun. 28, 2007

(65) Prior Publication Data
US 2009/0301873 A1 Dec. 10, 2009

(30) Foreign Application Priority Data
Dec. 21, 2005 (GB) .................................. 0526006.2
Jun. 14, 2006 (GB) .................................. 0611800.4

(51) Int. Cl.
*C07C 39/44* (2006.01)
(52) U.S. Cl.
USPC .............................. 556/136; 556/16; 556/137
(58) Field of Classification Search
USPC ............................................ 556/16, 136, 137
See application file for complete search history.

(56) References Cited

U.S. PATENT DOCUMENTS

| 3,901,712 | A | 8/1975 | Beavers |
| 4,207,305 | A | 6/1980 | Diamond et al. |
| 5,135,901 | A | 8/1992 | Beavers |
| 5,227,084 | A | 7/1993 | Martens et al. |
| 5,968,745 | A | 10/1999 | Thorp et al. |
| 7,341,846 | B2 | 3/2008 | Yamaoka et al. |
| 2001/0021514 | A1 | 9/2001 | Terpetschnig et al. |
| 2002/0049190 | A1 | 4/2002 | Bridger et al. |
| 2005/0250051 | A1* | 11/2005 | Kim et al. ..................... 430/322 |
| 2005/0272713 | A1 | 12/2005 | Brewer et al. |

FOREIGN PATENT DOCUMENTS

| GB | 1514805 | 6/1978 |
| JP | 10298592 | 11/1998 |
| JP | 2005-225834 | 8/2005 |
| WO | WO-9116719 | 10/1991 |
| WO | WO-9309124 | 5/1993 |
| WO | WO-9325562 | 12/1993 |
| WO | WO-9419449 | 9/1994 |
| WO | WO-9637593 | 11/1996 |
| WO | 9850393 | 11/1998 |
| WO | WO-9903868 | 1/1999 |
| WO | WO-02059122 | 8/2002 |
| WO | WO-02059157 | 8/2002 |
| WO | WO 03/097860 | 11/2003 |
| WO | WO-03093284 | 11/2003 |
| WO | WO-2004009604 | 1/2004 |
| WO | 2005026178 | 3/2005 |

OTHER PUBLICATIONS

Chou, M. et al. "Reactivity and coordination chemistry of aromatic carboxamide RC(O)NH2 and carboxylate ligands: properties of pentaammineruthenium(II) and -(III) complexes," Inorg. Chem. (1994) 33: 1674-1684.*

Man, et al., 2004. "Highly Electrophilic (Salen)ruthenium(VI) Nitrido Complexes". J. Am. Chem. Soc. 126: 478-479.

Lagref, et al., 2003. "Molecular Engineering on Semiconductor Surfaces: Design, Synthesis and Application of New Efficient Amphiphilic Ruthenium Photosensitizers for Nanocrystalline TiO2 Solar Cells". Synthetic Metals 138: 333-339.

Fedorova, et al., 2006. "Development of a Novel Enzyme-REdox-mediator System Based on a Fungal Laccase and Ruthenium Complexes". Applied Biochemistry and Microbiology 42(6): 550-557.

Seifriz et al., "Synthesis, potentiometric titration, electrochemical investigation and biological properites of trans-[RuCl$_2$(dinic)$_4$] (dinic = 3,5-pyridinecarboxylic acid)", *J. of Inorganic Biochemistry*, 1999; 76: 153-163.

Paula et al., "Synthesis, Electrochemical Characterization and Potentiometric Titration of trans-[RuCl$_2$(L)$_4$] Complexes (L = Pyridine Derived Ligands: 3-Pyridinecarboxylic Acid and 4-Pyridinecarboxylic Acid)", *J. Coord. Chem.*, 1999; 46: 491-504.

Balakaeva et al., "Complexes of Ruthenium (IV) with Nicotinic Acid", *Russian J. of Coord. Chem.*, 1997; 23(7): 502-506.

Shin et al., "Electroabsorption Spectroscopy of Charge-Transfer States of Transition-Metal Complexes. 2. Metal-to-Ligand and Ligand-to-Metal Charge-Transfer Excited States of Pentaammineruthenium Complexes", *J. Phys. Chem.*, 1996; 100: 8157-8169.

Tricarito et al., "Intramolecular isomerization of bifunctional ligands coordinated to pentaammineruthenium", *Acta Cientifica Venezolana*, 1986; 37(2): 209-213.

Neves et al., "Intramolecular Electron-Transfer Reactions in Bridged Polynuclear Ru$^{II}$-Co$^{III}$ Complexes Containing a (µ-Carboxylato)bis(µhydroxo)bis[(amine)cobalt(III)] (and a Ru$^{II}$(NH$_3$)$_5$) Structural Unit", *J. Am. Chem. Soc.*, 1986; 106: 5532-5537.

Zawacky and Taube, "Intramolecular Electron-Transfer Reaction in Bridged Binuclear Ru(II)-Co(III) Molecules", *J. Am. Chem. Soc.*, 1981; 103: 3379-3387.

Durrent et al., "Functionalising nanocrystalline TiO$_2$ films: dye sensitisation and protein immobilisation",Topical Issues in Glasses, 1999; 3 (Photons, Glasses, and Coatings): 68-74.

Fung, et al., 1998. "Chemoselective Oxidation of Alcohols to Aldehydes and Ketones by tert-Burtly Hydroperoxide Catalyzed by a Ruthenium Complex of N, N', N"-Trimethyl-1,4,7-triazacyclononane". J. Org. Chem 63: 2873-2877.

(Continued)

Primary Examiner — Johann R Richter
Assistant Examiner — Pancham Bakshi
(74) Attorney, Agent, or Firm — Krieg DeVault LLP

(57) ABSTRACT

The present application is generally directed to ruthenium or osmium containing complexes and their use as redox mediators in electrochemical biosensors.

14 Claims, 26 Drawing Sheets

(56) References Cited

OTHER PUBLICATIONS

Che, et al., 2000. "Alkyne Oxidations by cis-Dioxorutheniium(VI) Complexes. A Formal [3+2] Cycloaddition Reaction of Alkynes with cis-[(Cn*(CF$_3$CO$_2$)Ru$^{VI}$O$_2$]ClO$_4$ (Cn* = 1,4,7-Trimethyl-1,4,7-triazacyclononane)". J. Am. Chem. Soc. 122: 11380-11392.

Au, et al., 1998. "Ruthenium-mediated amidation of saturated C-H bonds and crystal structure of bis(tosyl)amidoruthenium(III) comples of 1,4,7-trimethyl-1,4,7-triazacyclononane". Chem. Commun., pp. 2677-2678.

Cheung, et al., 2005. "Oxidation of anisoles to p-benzoquinone monoketals catalyzed by a ruthenium complex of 1,4,7,-trimethyl-1,4,7-triazacyclononane with tert-butyl hydroperoxide". Can. J. Chem. 83: 521-526.

Cheung, et al., 2002. "A Silica Gel-Supported Ruthenium Complex of 1,4,7-Trimethyl-1,4,7-triazacyclononane as Recyclable Catalyst for Chemoselective Oxidation of Alcohols and Alkenes by tert-Butyl Hydroperoxide". J. Org. Chem. 67: 7716-7723.

Yip, et al., 2005. "Alkene cis-Dihydroxylation by [(Me$_3$tacn)(CF$_3$CO$_2$)Ru$^{VI}$O$_2$]ClO$_4$ (Me$_3$tacn = 1,4,7-trimethyl-1,4,7-triazacyclononane): Structural Characterization of [3+2] Cycloadducts and Kinetic Studies". J. Am. Chem. Soc. 127(41): 14239-14249.

Evans, et al., 1973. "Dichlorotetrakis(dimethyl sulphoxide)ruthenium(II) and its Use as a Source Material for Some New Ruthenium(II) Complexes". J. Chem. Soc., 1973, pp. 204-209.

Ford, et al., 1968. "Synthesis and Properties of Pentaamminepyridineruthenium(II) and Related Pentaamineruthenium Complexes of Aromatic Nitrogen Heterocycles". J. Am. Chem. Soc. 90(5): 1187-1194.

Malouf, et al., 1974. "Photochemical Reaction Pathways of Ruthenium(II) Complexes, Evidence Regarding the Reactive Excited State(s) from Metal-to-Ligand Charge Transfer Excitation of Ru(NH$_3$)$_{5py}^{2+}$ and Related Complexes". J. Am. Chem. Soc. 96(2): 601-603.

Malouf, et al., 1977. "Photochemistry of the Ruthenium(II) Ammine Complexes, Ru(NH$_3$)$_5$(py-X)$^{2+}$. Variation of Systemic Parameters to Modify Photochemical Reactivities". J. Am. Chem. Soc. 99(22): 7213-7221.

Schneider, et al., 1993. "Mononuclear and Dinuclear Ruthenium Complexes Containing the LRu(acac) Fragment. Crystal Structures of [LRu$^{III}$(acac)(OH)]PF$_6$•H$_2$O, [ILRu$^{III}$(acac)I$_2$(µ- O$_2$H$_3$)](PF$_6$)$_3$, and [ILRu$^{III}$(acac)I$_2$(µ-O)](PF$_6$)$_2$. Characterization of the Mixed-Valence Species [IRu$^{III}$(acac)I$_2$(µ-O)](PF$_6$)$_3$ (L = 1,4,7-trimethyl-1,4,7-triazacyclononane)". Inorg. Chem. 32: 4925-4934.

Lahiri, et al., 1987. "Ruthenium and Osmium Complexes of N$_2$O Chelators: Syntheses, Oxidation Levels, and Distortion Parameters". Inorg. Chem. 26(26): 4324-4331.

Neubold, et al., 1990. "Novel Cofacial Bioctahedral Complexes of Ruthenium: Syntheses and Properties of the Mixed-Valence Species [LRu$^{2.5}$(µ-X)$_3$Ru$^{2.5}$L]$^{2+}$ (X = Cl, Br, I, OH). Crystal Structures of [LRu$^{2.5}$(µ-OH)$_3$Ru$^{2.5}$L](PF$_6$)$_2$•H$_2$O and [LRu$^{IV}$(µ-O)$_3$Ru$^{IV}$L](PF$_6$)2•H$_2$O (L = 1,4,7,-trimethyl-1,4,7-triazacyclononane)". Inorg. Chem. 29: 3355-3363.

Ford, et al., 1976. "The Use of Ligand Substituents to Modify Photochemical Reactivities. Studies of Ruthenium(II) and Rhodium(III) Ammine Complexes". dvances in Chemistry Series 150: 187-200.

Dwyer, et al., 1963. "Mono- and bis-(2,2'-bipyridine) and -(1,10-phenanthroline) Chelates of Ruthenium and Osmium". Aust. J. Chem. 16: 544-548.

Buckingham, et al., 1964. "Mono- and bis-(2,2'-bipyridine) and -(1,10-phenanthroline) Chelates of Ruthenium and Osmium". Aust. J. Chem. 17: 325-336.

Forrow, et al., 2002. "The influence of structure in the reaction of electrochemically generated ferrocenium derivatives with reduced glucose oxidase". J. Chem. Soc., Dalton Trans., 3178-3194.

Matsubara, et al., 1976. "Some Applications of Cyclic Voltammetry to the Reactions and Properties of Ruthenium Ammine Complexes. Reduction Potentials and Rate Studies". Inorg. Chem. 15(5): 1107-1110.

Bernhard, et al., 1997. "Ligand Dehydration in Ruthenium-Amine Complexes: Reactivity of 1,2-Ethanediamine and 1,1,1-Tris(aminomethyl)ethane". Inorg. Chem. 36(13): 2804-2815.

Allen, et al., 1970. "Pentaammine(Nitrogen)Ruthenium(II) Salts and Other Ammines of Ruthenium". Inorganic Syntheses 12: 2-8.

Gaunder, et al., 1970. "The Reduction of Complexes of Pentaammineruthenium(III) with Pyridine Derivatives". Inorg. Chem. 9(12): 2627-2639.

Cheng, et al., 1996. "Chiral ruthenium(IV)-oxo complexes. Structure, reactivities of [Ru(terpy)(N∩N)O]$^{2+}$ (N∩N = N,N,N',N'-tetramethyl-1,2-diaminocyclohexane) and [Ru(Me$_3$tacn)(cbpy)O]$^{2+}$ (cbpy = (−)-3,3'-[(4S-trans)-1,3-dioxolane-4,5-dimethyl]-2,2'-bypyridine)". Inorganica Chimica Acta 242: 105-113.

Yip, et al., 2008. "Homogeneous [Ru$^{III}$(Me$_3$tacn)Cl$_3$]-Catalyzed Alkene cis-Dihydroxylation with Aqueous Hydrogen Peroxide". Chem. Asian J. 3: 70-77.

Allen et al., Inorganic Syntheses Ammines of Ruthenium, 3-9, vol. 12; 2007.

Chan et al., J. Chem. Soc., Dalton Trans., 1999, 3197-3201.

Cheng, et al., Inorganica Chimica Acta 272, 1998 176-187.

* cited by examiner

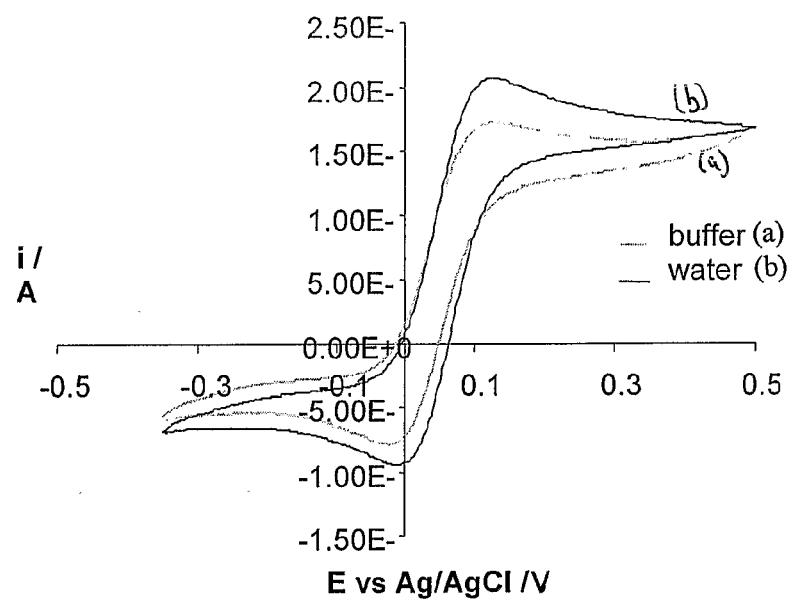
Figure 3
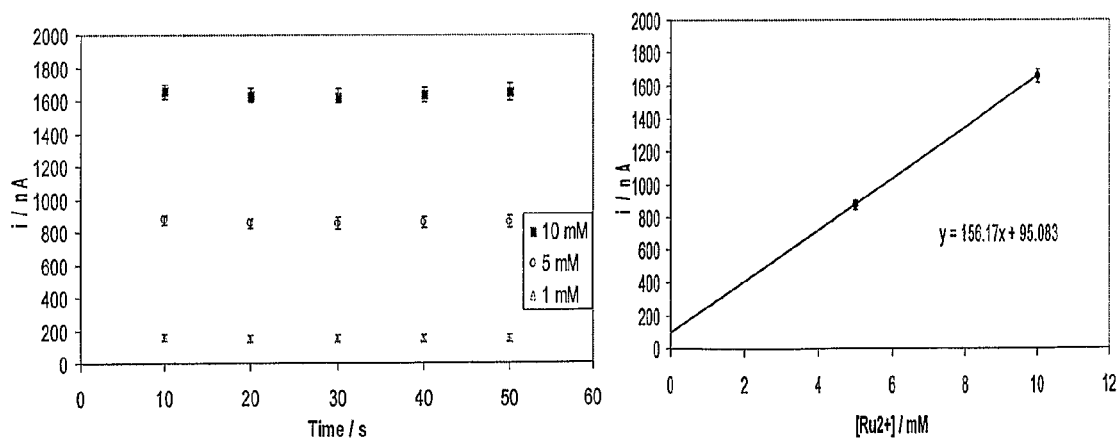
Figure 4a
Figure 4b

| Ligand (L) | X | Y | Ligand | X | Y |
|---|---|---|---|---|---|
| 4-pyridinecarboxylic acid (COOH at 4-position of pyridine) | 5 | 1 | 4-pyridinecarboxylic acid | 4 | 2 |
| pyridine-3,5-dicarboxylic acid | 5 | 1 | pyridine-3,5-dicarboxylic acid | 4 | 2 |
| 2,2'-bipyridine-4-carboxylic acid | 4 | 1 | 2,2'-bipyridine-4,4'-dicarboxylic acid | 4 | 1 |
| 1,10-phenanthroline-3-carboxylic acid | 4 | 1 | 1,10-phenanthroline-3,8-dicarboxylic acid | 4 | 1 |

$[Ru^{3+}(NH_3)_x(L)_y]^z$ where X and Y are as given above, Z = effective charge in solution = $(3-m)+$, at pH 7-9, and m = no of carboxylic acids in the complex. When not in solution, the overall charge will be 3+

Figure 41

REDOX MEDIATORS

CROSS REFERENCE TO RELATED APPLICATIONS

This application is a U.S. national phase of PCT/GB2006/004855 filed Dec. 21, 2006, and claims the benefit of British Patent Applications No. 0526006.2 filed on Dec. 21, 2005, and 0611800.4 filed on Jun. 14, 2006, all of which are incorporated by reference herein. The International application published in English on Jun. 28, 2007 as WO 2007/072018 A2.

The present invention relates to novel ruthenium or osmium complexes and their use in biosensors. In particular the invention relates to the use of ruthenium complexes having an overall charge on the ruthenium-containing species less than 3+ in the ruthenium(III) state as redox mediators.

Biosensors are analytical tools combining a biochemical recognition component or sensing element with a physical transducer. They have wide application in such diverse fields as personal health monitoring, environmental screening and monitoring, bioprocess monitoring, and within the food and beverage industry.

The biological sensing element can be an enzyme, antibody, DNA sequence, or even microorganism. The biochemical component serves to selectively catalyze a reaction or facilitate a binding event. The selectivity of the biochemical recognition event allows for the operation of biosensors in a complex sample matrix, i.e., a body fluid. The transducer converts the biochemical event into a measurable signal, thus providing the means for detecting it. Measurable events range from spectral changes, which are due to production or consumption of an enzymatic reaction's product/substrate, to mass change upon biochemical complexation.

In general, transducers take many forms and they dictate the physicochemical parameter that will be measured. Thus, the transducer may be optically-based, measuring such changes as optical absorption, fluorescence, or refractive index. It may be mass-based, measuring the change in mass that accompanies a biologically derived binding reaction. Additionally, it may be thermally based (measuring the change in enthalpy (heat) or amperometry or impedance based (measuring the change in electrical properties) that accompanies the analyte/bio-recognition layer interaction.

Biosensors offer the convenience and facility of distributed measurement, that is, the potential ability to take the assay to the point of concern or care. Properly designed and manufactured, biosensor devices may be conveniently mass-produced.

There are, however, several limitations to the use of biosensors. These include a vulnerability of the transducer to foulants and interferences.

Enzyme based biosensors are widely used in the detection of analytes in clinical, environmental, agricultural and biotechnological applications. Analytes that can be measured in clinical assays of fluids of the human body include, for example, glucose, lactate, cholesterol, bilirubin and amino acids. Levels of these analytes in biological fluids, such as blood, are important for the diagnosis and the monitoring of diseases.

The sensors which can are generally used in enzyme based systems are provided as either point of care or over the counter devices. They can be used to test fresh, unmodified, finger prick whole blood samples, to determine the concentrations of total cholesterol, triglycerides, HDL and LDL within 1 to 2 minutes of adding the sample to a device (note: this time is not fixed and could be subject to significant variations). These four parameters, in combination, have been clinically proven to give a very good indication of the risk of heart disease in adults. It is well known that high cholesterol is asymptomatic thus it is recommended that every adult should have a test to assess their risk. If their risk is found to be high it can be significantly reduced by correct management of either diet alone, or in combination with therapeutic drugs.

In one example of such an enzyme based biosensor there is utilised an electrochemical assay to detect the analyte in question. Use is made of a change in the oxidation state of a mediator which interacts with an enzyme which has reacted with the analyte to be determined. The oxidation state of the mediator is chosen so that it is solely in the state which will interact with the enzyme on addition of the substrate. The analyte reacts with the stoichiometric concentration of the mediator via the enzyme. This causes the mediator to be oxidised or reduced (depending on the enzymatic reaction) and this change in the level of mediator can be measured by determining the current generated at a given potential.

Electrochemical assays are typically performed in cells with two or three electrodes, including at least one measuring or working electrode and one reference electrode. In three electrode systems, the third electrode is a counter-electrode. In two electrode systems, the reference electrode also serves as the counter-electrode. The electrodes are connected through a circuit, such as a potentiostat. The measuring or working electrode is a carbon or metal conductor. Upon passage of a current through the working electrode, a redox enzyme is electrooxidized or electroreduced. The enzyme is specific to the analyte to be detected, or to a product of the analyte. The turnover rate of the enzyme is typically related (preferably, but not necessarily, linearly) to the concentration of the analyte itself, or to its product, in the test solution.

The electrooxidation or electroreduction of the enzyme is often facilitated by the presence of a redox mediator in the solution or on the electrode. The redox mediator generally assists in the electrical communication between the working electrode and the enzyme. The redox mediator can be dissolved in the fluid to be analyzed, which is in electrolytic contact with the electrodes. Useful devices can be made, for example, by coating an electrode with a film that include a redox mediator and an enzyme where the enzyme is catalytically specific to the desired analyte, or its products. A diffusional redox mediator, which can be soluble or insoluble in water, functions by shuttling electrons between, for example, the enzyme and the electrode. In any case, when the substrate of the enzyme is electrooxidized, the redox mediator transports electrons from the substrate-reduced enzyme to the electrode; when the substrate is electroreduced, the redox mediator transports electrons from the electrode to the substrate-oxidized enzyme.

Many previously used enzyme based electrochemical sensors have employed a number of different redox mediators such as monomeric ferrocenes, quinoid-compounds including quinines (e.g. benzoquinones), nickel cyclamates, and ruthenium amines. For the most part, these redox mediators have one or more of the following limitations; the solubility of the redox mediators in the test solutions is low, their chemical, light, thermal, or pH stability is poor, or they do not exchange electrons rapidly enough with the enzymes or the electrode or both. Additionally, the redox potential of many of these reported redox mediators are so oxidizing that at the potential where the reduced mediator is electrooxidized on the electrode, solution components other than the analyte are also electrooxidized; in other cases they are so reducing that the solution components, such as, for example, dissolved oxygen are also rapidly electroreduced. As a result, the sensor utilizing the mediator is not sufficiently specific.

Ruthenium based complexes have previously been utilised as redox mediators in reactions containing, for example, cholesterol dehydrogenase. For example any $[Ru^{II}(NH_3)_6]^{2+}$ species which is present is converted to $[Ru^{III}(NH_3)_6]^{3+}$ at an electrode poised at a suitable potential: the current passed is proportional to the amount of $Ru^{II}(NH_3)_6$ species formed via the enzymatic reaction. However, such a highly-charged species as $[Ru^{III}(NH_3)_6]^{3+}$ forms, to a greater or lesser extent, complexes, usually in the form of ion-pairs, with negatively-charged groups on enzymes and the electrode surface thus impeding the reactions necessary for the analytical process to occur effectively and efficiently.

It would, therefore, be desirable to utilise a redox mediator which forms less strong complexes or none at all with the components of the analytical mixture and the electrode and thus lead to measured responses from said mediators being more reliable, stable and reproducible.

According to a first aspect of the present invention there is provided the use of a complex of Formula I

$[M(A)_x(B)_y]^m(X^z)_n$   Formula I as a redox mediator wherein M is ruthenium or osmium and has an oxidation state of 0, 1, 2, 3 or 4;

x, and n are independently an integer selected from 1 to 6; y is an integer selected from 1 to 5; m is an integer from −5 to +4 and z is an integer from −2 to +1;

A is a mono- or bidentate aromatic ligand containing 1 or 2 nitrogen atoms;

B is independently selected to be any suitable ligand other than a heterocyclic nitrogen-containing ligand;

X is any suitable counter ion;

wherein A is optionally substituted by 1 to 8 groups independently selected from substituted or unsubstituted alkyl, alkenyl, or aryl groups, —F, —Cl, —Br, —I, —$NO_2$, —CN, —$CO_2H$, —$SO_3H$, —$NHNH_2$, —SH, alkoxycarbonyl, alkylaminocarbonyl, dialkylaminocarbonyl, —OH, alkoxy, —$NH_2$, alkylamino, dialkylamino, alkanoylamino, arylcarboxamido, alkylhydrazino, hydroxylamino, alkoxyamino, alkylthio;

wherein the number of coordinating atoms is 6.

The ligand A can be a monodentate ligand substituted by one or more $CO_2R^2$ groups, or a bi- or tridentate ligand optionally substituted by one or more $CO_2R^2$ groups The group $R^2$ can be selected to be H.

The ligand A can be selected from nicotinic acid, isonicotinic acid, 2,2'-bipyridine, 2,2-bipyridine-5,5'-dicarboxylic acid, 2,2-bipyridine-4,4'-dicarboxylic acid, or 5-chloro-8-hydroxyquinoline.

According to a second aspect of the present invention there is provided the use of a complex of Formula II

$[M(A)_x(B)_y]^m(X^z)_n$   Formula II as a redox mediator wherein M is ruthenium or osmium and has an oxidation state of 0, 1, 2, 3 or 4;

x, and n are independently an integer selected from 1 to 6; y is an integer selected from 0 to 5; m is an integer from −5 to +4 and z is an integer from −2 to +1;

A is a bi-, tri-, terra-, penta- or hexadentate ligand which can be either linear having the formula $R^1RN(C_2H_4NR)_wR^1$ or cyclic having the formulae $(RNC_2H_4)_v$, $(RNC_2H_4)_p(RNC_3H_6)_q$, or $[(RNC_2H_4)(RNC_3H_6)]_s$, wherein w is an integer from 1 to 5, v is an integer from 3 to 6, p and q are integers from 1 to 3 whereby the sum of p and q is 4, 5 or 6, and s is either 2 or 3, and wherein R and $R^1$ are either hydrogen or methyl;

B is independently selected to be any suitable ligand;

X is any suitable counter ion;

wherein B is optionally substituted by 1 to 8 groups independently selected from substituted or unsubstituted alkyl, alkenyl, or aryl groups, —F, —Cl, —Br, —I, —$NO_2$, —CN, —$CO_2H$, —$SO_3H$, —$NHNH_2$, —SH, alkoxycarbonyl, alkylaminocarbonyl, dialkylaminocarbonyl, —OH, alkoxy, —$NH_2$, alkylamino, dialkylamino, alkanoylamino, arylcarboxamido, alkylhydrazino, hydroxylamino, alkoxyamino, alkylthio;

wherein the number of coordinating atoms is 6.

The ligand A can be a bi-, tri- or tetradentate ligand which can be either linear having the formula $R^1RN(C_2H_4NR)_wR^1$ or cyclic having the formulae $(RNC_2H_4)_v$, $(RNC_2H_4)_p(RNC_3H_6)_q$, $[(RNC_2H_4)(RNC_3H_6)]_s$; wherein w is an integer from 1 to 3, v is either 3 or 4, p and q are integers from 1 to 3 whereby the sum of p and q is 4, and s is either 2 or 3;

The ligand A can be selected from 1,4,7-trimethyl-1,4,7-triazacyclononane, or 1,1,4,7,10,10-hexamethyltriethylenetetramine, 1,2-dimethylethylenediamine, or 1,1,2,2-tetramethylethylenediamine.

The ligand B in Formula I or Formula II can be selected from amine ligands such as $NH_3$ or from CO; CN; halogen, and acetylacetonate (acac), 3-bromo-acetylacetonate (Bracac), oxalate, pyridine, or 5-chloro-8-hydroxyquinoline.

The ligands A and B in either Formula I or Formula II can be selected to be bidentate, and the geometry of the complex cis or trans.

The oxidation state of the metal in the complexes of either Formula I or Formula II can be selected to be 2+, 3+ or 4+.

The oxidation state of the metal in the complexes of either Formula I or Formula II can be selected to be 3+.

The ligands A and B in either Formula I or Formula II can be selected from the group +2, +1, 0, −1, −2 and −3.

The counterion in the complexes of Formula I or Formula II can be selected from $F^-$, $Cl^-$, $Br^-$, $I^-$, $NO_3^-$, $NH_4^+$, $NR_4^+$, $PF_6^-$, $CF_3SO_3^-$, $SO_4^{2-}$, $ClO_4^-$, $K^+$, $Na^+$, $Li^+$. A combination of counterions can be used.

The complex of Formula I or Formula II can be selected from $[Ru^{III}(NH_3)_5(pyridine-3-COOH)](PF_6)_2(CF_3SO_3)$, $[Ru^{III}(2,4-pentandionate)_2(pyridine-3-COOH)(pyridine-3-COO)]$, $[Ru^{III}(3-bromo-2,4-pentandionate)_2(pyridine-3-COOH)(pyridine-3-COO)]$, $[Ru^{III}(2,4-pentandionate)_2(2,2'-bipyridine-5,5'-(COOH)(COO)]$, $[Ru^{III}(2,4-pentandionate)_2(2,2'-bipyridine-4,4'-(COOH)(COO)]$, $[Ru^{III}(2,4-pentandionate)_2(2,2'-bipyridine)]Cl$, $[Ru^{III}(2,4-pentandionate)_2(pyridine-4-COOH)(pyridine-4-COO)]$, $[Ru^{III}(5-chloro-8-hydroxyquinoline)_2(pyridine-3-COOH)(pyridine-3-COO)]$, $[Ru^{III}(1,1,4,7,10,10-hexamethyltriethylenetetramine)(2,4-pentandionate)](PF_6)(CF_3SO_3)$, $[Ru^{III}(1,1,4,7,10,10-hexamethyltriethylenetetramine)(2,4-pentandionate)]Cl_2$, $[Os^{II}(2,2'bipyridine)_2(2,4-pentandionate)]Cl$, $[Ru^{II}(2,2'bipyridine)_2(2,4-pentandionate)]Cl$, $[Ru^{II}(2,2'bipyridine)_2(C_2O_4)]$, $K[Ru^{III}(C_2O_4)_2(pyridine-3-COOH)_2]$, $[Ru^{III}(1,4,7-trimethyl-1,4,7-triazacyclononane)(2,4-pentandionate)(pyridine)](NO_3)_2$.

The complex of Formula I or Formula II can be selected from $[Ru^{III}(2,4-pentandionate)_2(pyridine-3-COOH)(pyridine-3-COO)]$, $[Ru^{III}(1,4,7-trimethyl-1,4,7-triazacyclononane)(2,4-pentandionate)(pyridine)](NO_3)_2$, or $[Ru^{III}(1,1,4,7,10,10-hexamethyltriethylenetetramine)(2,4-pentandionate)]Cl_2$.

The redox mediator can be used in an electrochemical sensor. The electrochemical sensor can include a microband electrode. The electrochemical sensor can be an electrochemical biosensor. The electrochemical biosensor can be used to detect analytes in body fluids, environmental samples, foods and beverages, veterinary samples, pharmaceuticals.

According to a third aspect of the present invention there is provided the use of a ruthenium complex of Formula I or Formula II as previously defined in a biosensor.

The complex of Formula I or Formula II can be used at a pH of 6 to 10. The complex of Formula I or Formula II can be used at a pH of 7 to 9.

The biosensor can be used with any compatible biochemical analyte. The analyte can be found in a biological fluid, and can also be selected from any of an enzyme, enzyme substrate, antigen, antibody, nucleic acid sequence, cholesterol, cholesterol esters, lipoproteins, triglycerides or a microorganism.

According to a fourth aspect of the present invention there is provided a detection system for measuring an analyte comprising:
(a) contacting a sample which contains the analyte with solution containing a redox mediator selected from a group of Ru-containing or Os-containing compounds according to Formula I or Formula II;
(b) incubating the contacted sample under conditions that cause the enzyme to act on the analyte;
(c) subjecting the incubated sample of step (b) to conditions which result in a change in a measurable signal; and
(d) measuring the resulting signal.

The measurable signal can be an electrochemical, colourimetric, thermal, impedometric, capacitive or spectroscopic signal. The measurable signal can be an electrochemical signal measured at a microband electrode.

According to a fifth aspect of the present invention there is provided a complex according to Formula I

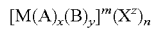  Formula I wherein M is ruthenium or osmium and has an oxidation state of 0, 1, 2, 3 or 4;
x, and n are independently an integer selected from 1 to 6;
y is an integer selected from 1 to 5; m is an integer from −5 to +4 and z is an integer from −2 to +1;
A is a mono- or bidentate aromatic ligand containing 1 or 2 nitrogen atoms;
B is independently selected to be one or more of any suitable ligand other than a heterocyclic nitrogen-containing ligand;
X is any suitable counter ion;
wherein A is optionally substituted by 1 to 8 groups independently selected from substituted or unsubstituted alkyl, alkenyl, or aryl groups, —F, —Cl, —Br, —I, —NO$_2$, —CN, —CO$_2$H, —SO$_3$H, —NHNH$_2$, —SH, alkoxycarbonyl, alkylaminocarbonyl, dialkylaminocarbonyl, —OH, alkoxy, —NH$_2$, alkylamino, dialkylamino, alkanoylamino, arylcarboxamido, alkylhydrazino, hydroxylamino, alkoxyamino, alkylthio;
wherein the number of coordination atoms is 6.

The ligand A can be a monodentate ligand substituted by one or more CO$_2$R$^2$ groups, or a bi- or tridentate ligand optionally substituted by one or more CO$_2$R$^2$ groups wherein said one or more CO$_2$R$^2$ groups. R$^2$ can be selected to be H.

The ligand A can be selected from nicotinic acid, isonicotinic acid, 5-carboxy-nicotinic acid, 6-pyridyl-nicotinic acid, 2,2'-bipyridine-5,5'-bis-carboxylic acid, 2,2'-bipyridine-4,4'-bis-carboxylic acid, 2,2'-bipyridine, 1,10-phenanthroline-3,9-bis-carboxylic acid, According to a sixth aspect of the present invention there is provided a complex according to Formula II

[M(A)$_x$(B)$_y$]$^m$(X$^z$)$_n$  Formula II wherein M is ruthenium or osmium and has an oxidation state of 0, 1, 2, 3 or 4;
x, and n are independently an integer selected from 1 to 6;
y is an integer selected from 0 to 5; m is an integer from −5 to +4 and z is an integer from −2 to +1;
A is a bi-, tri-, terra-, penta- or hexadentate ligand which can be either linear having the formula R$^1$RN(C$_2$H$_4$NR)$_w$R$^1$ or cyclic having the formulae (RNC$_2$H$_4$)$_v$, (RNC$_2$H$_4$)$_p$ (RNC$_3$H$_6$)$_q$, or [(RNC$_2$H$_4$)(RNC$_3$H$_6$)]$_s$; wherein w is an integer from 1 to 5, v is an integer from 3 to 6, p and q are integers from 1 to 3 whereby the sum of p and q is 4, and s is either 2 or 3, and wherein R and R$^1$ are either hydrogen or methyl;
B is independently selected to be any suitable ligand;
X is any suitable counter ion;
wherein A is optionally substituted by 1 to 7 groups independently selected from substituted or unsubstituted alkyl, alkenyl, or aryl groups —F, —Cl, —Br, —I, —NO$_2$, —CN, —CO$_2$H, —SO$_3$H, —NHNH$_2$, —SH, alkoxycarbonyl, alkylaminocarbonyl, dialkylaminocarbonyl, —OH, alkoxy, —NH$_2$, alkylamino, dialkylamino, alkanoylamino, arylcarboxamido, alkylhydrazino, hydroxylamino, alkoxyamino, alkylthio;
wherein the number of coordinating atoms is 6.

The ligand A can be a bi-, tri-, tetradentate ligand which can be either linear having the formula R$^1$RN(C$_2$H$_4$NR)$_w$R$^1$ or cyclic having the formulae (RNC$_2$H$_4$)$_v$, (RNC$_2$H$_4$)$_p$ (RNC$_3$H$_6$)$_q$, [(RNC$_2$H$_4$)(RNC$_3$H$_6$)]$_s$; wherein w is an integer from 1 to 3, v is either 3 or 4, p and q are integers from 1 to 3 whereby the sum of p and q is 4, and s is either 2 or 3.

The ligand A can be selected from 1,4,7-trimethyl-1,4,7-triazacyclononane, or 1,1,4,7,10,10-hexamethyltriethylenetetramine, 1,2-dimethylethylenediamine, or 1,1,2,2-tetramethylethylenediamine.

The ligand B can be selected from amine ligands such as NH$_3$ or NMe$_3$ from CO, CN, halogen, acetylacetonate (acac), 3-bromo-acetylacetonate (Bracac), oxalate, 1,4,7-triethylene crown ether, oxalate, or 5-chloro-8-hydroxyquinoline.

The geometry of the complex can be cis or trans when ligands A or B are selected to be bi-dentate.

The oxidation state of the metal in the complexes of Formula I or Formula II can be selected to be 2+ or 3+. The oxidation state of the metal in the complexes of Formula I or Formula II can be selected to be 3+.

The ligands A and B can be selected such that the overall charge on the complex of Formula I or Formula II is selected from the group +2, +1, 0, −1, −2 and −3.

The counter ion can be selected from F$^-$, Cl$^-$, Br$^-$, I$^-$, NO$_3^-$, NH$_4^+$, NR$_4^+$, PF$_6^-$, CF$_3$SO$_3^-$, SO$_4^{2-}$, ClO$_4^-$, K$^+$, Na$^+$, Li$^+$. A combination of counterions can be used.

The complex of Formula I or Formula II can be selected to be [Ru$^{III}$(NH$_3$)$_5$(pyridine-3-COOH)](PF$_6$)$_2$(CF$_3$SO$_3$), [Ru$^{III}$(2,4-pentandionate)$_2$(pyridine-3-COOH)(pyridine-3-COO)], [Ru$^{III}$(3-bromo-2,4-pentandionate)$_2$(pyridine-3-COOH)(pyridine-3-COO)], [Ru$^{III}$(2,4-pentandionate)$_2$(2,2'-bipyridine-5,5'-(COOH)(COO)], [Ru$^{III}$(2,4-pentandionate)$_2$(2,2'-bipyridine-4,4'-(COOH)(COO)], [Ru$^{III}$(2,4-pentandionate)$_2$(2,2'-bipyridine)]Cl, [Ru$^{III}$(2,4-pentandionate)$_2$(pyridine-4-COOH)(pyridine-4-COO)], [Ru$^{III}$(5-chloro-8-hydroxyquinoline)$_2$(pyridine-3-COOH)(pyridine-3-COO)], [Ru$^{III}$(1,1,4,7,10,10-hexamethyltriethylenetetramine)(2,4-pentandionate)](PF$_6$)(CF$_3$SO$_3$), [Ru$^{III}$(1,1,4,7,10,10-hexamethyltriethylenetetramine)(2,4-pentandionate)]Cl$_2$, [Os$^{II}$(2,2'-bipyridine)$_2$(2,4- pentandionate)]Cl, [Ru$^{II}$(2,2'-bipyridine)$_2$(2,4-pentandionate)]Cl, [Ru$^{II}$(2,2'-bipyridine)$_2$(C$_2$O$_4$)], K[Ru$^{III}$(C$_2$O$_4$)$_2$(pyridine-3-COOH)$_2$], [Ru$^{III}$(1,4,7-trimethyl-1,4,7-triazacyclononane)(2,4-pentandionate)(pyridine)](NO$_3$)$_2$.

It should be understood that in each of the complexes of Formula I or Formula II the metal can be selected to be ruthenium or osmium as required. In addition, the metals in the specific complexes described above can be changed to form the corresponding ruthenium or osmium complex. A person skilled in the art will appreciate that substituting the Ru with Os in a complex will change the working potential of that complex by around −400 mV to −600 mV and that the working potential can be further fine tuned, in the reverse direction if necessary, by altering the ligands around the metal centre, until the mediator reaches a working potential of −300 mV to +300 mV vs Ag/AgCl.

For example:

[Ru$^{III}$(acac)$_2$(py-3-COOH)(py-3-COO)] has an $E_{1/2}$ potential of −175 mV. [Ru$^{III}$(3-Bracac)$_2$(py-3-COOH)(py-3-COO)] is similar to [Ru$^{III}$(acac)$_2$(py-3-COOH)(py-3-COO)], but has bromo acac in place of acac and had an $E_{1/2}$ potential of −142 mV.

[Ru$^{III}$(acac)$_2$(py-4-COOH)(py-4-COO)] is similar to [Ru$^{III}$(acac)$_2$(py-3-COOH)(py-3-COO)], but has the COOH in a different place (py-4-COOH instead of py-3-COOH) and has an $E_{1/2}$ potential of −165 mV. A person skilled in the art will understand that the working potential has to be approximately 150 mV above $E_{1/2}$.

The complexes corresponding to the Ru complexes described herein are: [Os$^{III}$(NH$_3$)$_5$(pyridine-3-COOH)](PF$_6$)$_2$(CF$_3$SO$_3$), [Os$^{III}$(2,4-pentandionate)$_2$(pyridine-3-COOH)(pyridine-3-COO)], [Os$^{III}$(3-bromo-2,4-pentandionate)$_2$(pyridine-3-COOH)(pyridine-3-COO)], [Os$^{III}$(2,4-pentandionate)$_2$(2,2'-bipyridine-5,5'-(COOH)(COO)], [Os$^{III}$(2,4-pentandionate)$_2$(2,2'-bipyridine-4,4'-(COOH)(COO)], [Os$^{III}$(2,4-pentandionate)$_2$(2,2'-bipyridine)]Cl, [Os$^{III}$(2,4-pentandionate)$_2$(pyridine-4-COOH)(pyridine-4-COO)], [Os$^{III}$(5-chloro-8-hydroxyquinoline)$_2$(pyridine-3-COOH)(pyridine-3-COO)], [Os$^{III}$(1,1,4,7,10,10-hexamethyltriethylenetetramine)(2,4-pentandionate)](PF$_6$)(CF$_3$SO$_3$), [Os$^{III}$(1,1,4,7,10,10-hexamethyltriethylenetetramine)(2,4-pentandionate)]Cl$_2$, [Os$^{II}$(2,2'bipyridine)$_2$(2,4-pentandionate)]Cl, [Os$^{II}$(2,2'-bipyridine)$_2$(C$_2$O$_4$)], K[Os$^{III}$(C$_2$O$_4$)$_2$(pyridine-3-COOH)$_2$], [Os$^{III}$(1,4,7-trimethyl-1,4,7-triazacyclononane)(2,4-pentandionate)(pyridine)](NO$_3$)$_2$ When used herein, the following definitions define the stated term:

The term "alkyl" includes linear or branched, saturated aliphatic hydrocarbons. Examples of alkyl groups include methyl, ethyl, n-propyl, n-propyl, isopropyl, n-butyl, tert-butyl, cyclopentyl and the like. Unless otherwise noted, the term "alkyl" includes both alkyl and cycloalkyl groups.

The term "alkoxy" described an alkyl group joined to the remainder of the structure by an oxygen atom. Examples of alkoxy groups include methoxy, ethoxy, n-propoxy, isopropoxy, butoxy, tert-butoxy, cyclopentoxy, and the like. In addition, unless otherwise noted, the term "alkoxy" includes both alkoxy and cycloalkoxy groups.

The term "alkenyl" describes an unsaturated, linear or branched aliphatic hydrocarbon having at least one carbon-carbon double bond. Examples of alkenyl groups include ethenyl, 1-propenyl, 2-propenyl, 1-butenyl, 2-methyl-1-propenyl, cyclopentenyl and the like. In addition, unless otherwise noted, the term "alkenyl" includes both alkenyl and cycloalkenyl groups.

A "reactive group" is a functional group of a molecule that is capable of reacting with another compound to couple at least a portion of that other compound to the molecule. Reactive groups include carboxy, activated ester, sulfonyl halide, sulfonate ester, isocyanate, isothiocyanate, epoxide, aziridine, halide, aldehyde, ketone, amino, acrylamide, thiol, acyl azide, acyl halide, hydrazine, hydroxylamine, alkyl halide, imidazole, pyridine, phenol, alkyl, sulfonate, halotriazine, imido ester, maleimide, hydrazide, hydroxy, and photo-reactive azido aryl groups. Activated esters, as understood in the art, generally include esters of succinimidyl, benzotriazolyl, or aryl substituted by electron with drawing groups such as sulfo, nitro, cyano, or halo groups.

The term "acac" refers to the acetylacetonate anion which is the conjugate base of 2,4-pentanedione.

A "substituted" functional group (e.g., substituted alkyl, alkenyl, or alkoxy group) includes at least one substituent selected from the following: halogen, alkoxy, mercapto, aryl, alkoxycarbonyl, alkylaminocarbonyl, dialkylaminocarbonyl, —OH, —NH$_2$, alkylamino, dialkylamino, trialkylammonium, alkanoylamino, dialkanoylamino, arylcarboxamido, hydrazino, alkylthio, alkenyl and reactive groups.

A "biological fluid" is any body fluid or body fluid derivative in which the analyte can be measured, for example, blood, interstitial fluid, plasma, dermal fluid, sweat and tears.

An "electrochemical sensor" is a device configured to detect the presence of or measure the concentration or amount of an analyte in a sample via electrochemical oxidation or reduction reactions. These reactions typically can be transduced to an electrical signal that can be correlated to an amount or concentration of analyte.

A "redox mediator" is an electron transfer agent for carrying electrons between an analyte or an analyte-reduced or analyte-oxidized enzyme and an electrode, either directly or via one or more additional electron transfer agents.

"Electrolysis" is the electrooxidation or electroreduction of a compound either directly at an electrode or via one or more electron transfer agents (e.g., redox mediators or enzymes).

The term "reference electrode" includes both a) a reference electrode and b) a reference electrode that can also function as counter electrode (i.e. counter/reference electrodes), unless otherwise indicated.

The term "counter electrode" includes both a) a counter electrode and b) a counter electrode that can also function as a reference electrode (i.e., counter-reference electrode), unless otherwise indicated.

The term "measurable signal" means a signal which can be readily measured such as electrode potential, fluorescence, spectroscopic absorption, luminescence, light scattering, NMR, IR, mass spectroscopy, heat change, or a piezo-electric change.

The term "biochemical analyte" includes any measurable chemical or biochemical substance that may be present in a biological fluid and also includes any of an enzyme, an antibody, a DNA sequence, or a microorganism.

Monodentate, bidentate and tridentate, in accordance with the present invention have their generally accepted meaning in the art. That is, a monodentate ligand is defined as a chemical moiety or group that has one potential coordinating atom. More than one potential coordinating atom is termed a multidentate ligand where the number of potential coordinating atoms is indicated by the terms bidentate, tridentate, etc.

Known biosensors that can be used in accordance with the present invention may consist of, for example, a strip with four reagent wells and a common pseudo reference; with each well having its own tubular micro-band working electrode. The sensing component of the strip is provided by drying different, specially formulated, reagents comprising at an enzyme and a mediator that will interact with specific analytes in the test sample in each well. Since, potentially, different reagents can be added and dried to each well it is clear that it is possible to complete multi-analyte testing using a single test sample. The number of wells is variable, thus the number of unique tests is variable, for example sensors using between 1 and 6 wells may be used.

Conventional microelectrodes, typically with a working microelectrode and a reference electrode can be used. The working electrode is usually made of palladium, platinum, gold or carbon. The counter electrode is typically carbon, Ag/AgCl, Ag/Ag$_2$SO$_4$, palladium, gold, platinum, Cu/CuSO$_4$, Hg/HgO, Hg/HgCl$_2$, Hg/HgSO$_4$ or Zn/ZnSO$_4$.

In a preferred microelectrode the working electrode is in a wall of a receptacle forming said microelectrode. Examples of microelectrodes which can be used in accordance with the present invention are those disclosed in WO 03/097860.

Embodiments of the present invention will now be described by way of example only and with reference to the accompanying Figures, in which:

FIG. 3 shows cyclic voltammetry of the new mediator [Ru$^{II}$(py-$_3$COOH)(NH$_3$)$_5$](PF$_6$)$_2$ in 0.1 M pH9 Tris buffer (containing 0.1 M KCl) (a), and in a 0.1 M KCl solution (made with water) (b);

FIG. 4a shows repeat oxidative testing (at +0.25 V vs Ag/AgCl) of new mediator [Ru$^{II}$(py-$_3$COOH)(NH$_3$)$_5$](PF$_6$)$_2$ in 0.1 M KCl recorded in oxygenated environments. FIG. 4b shows Ru$^{2+}$ calibration data for mediator concentration with current;

Figure 28:
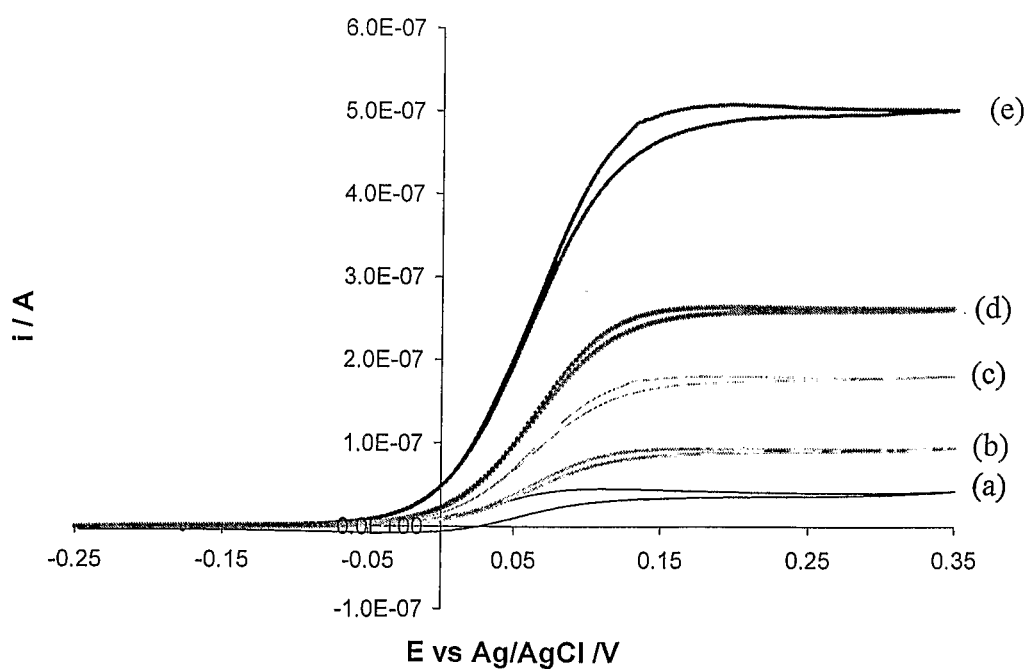
Figure 29:
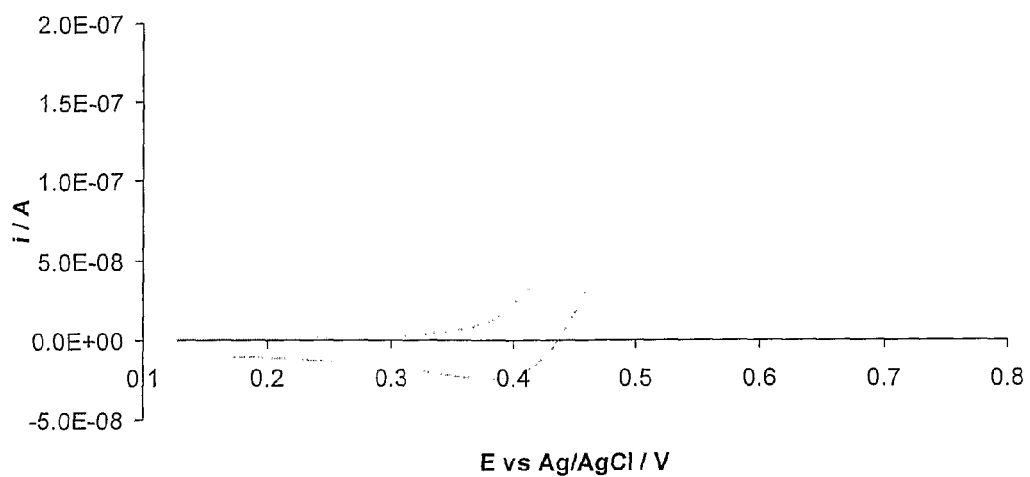
Figure 30:
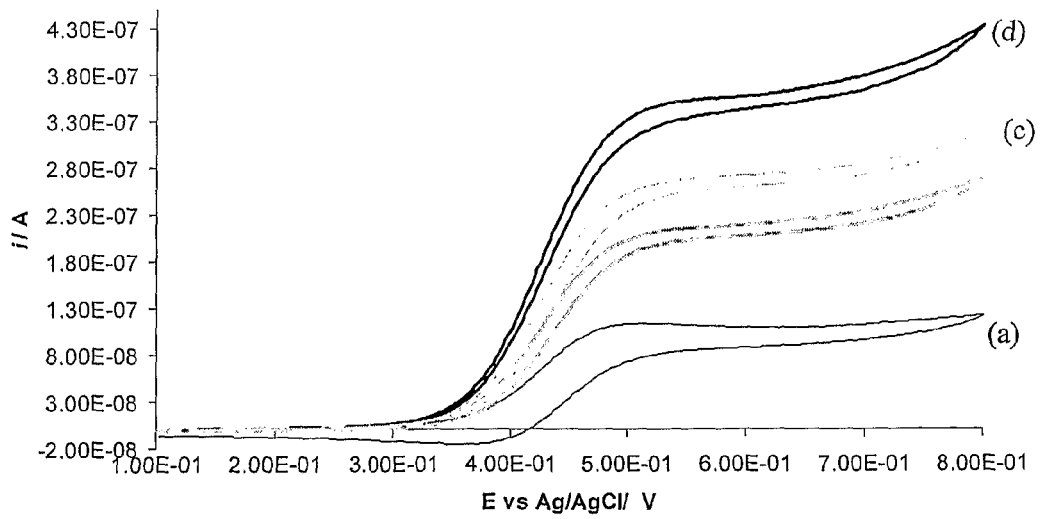
Figure 31:
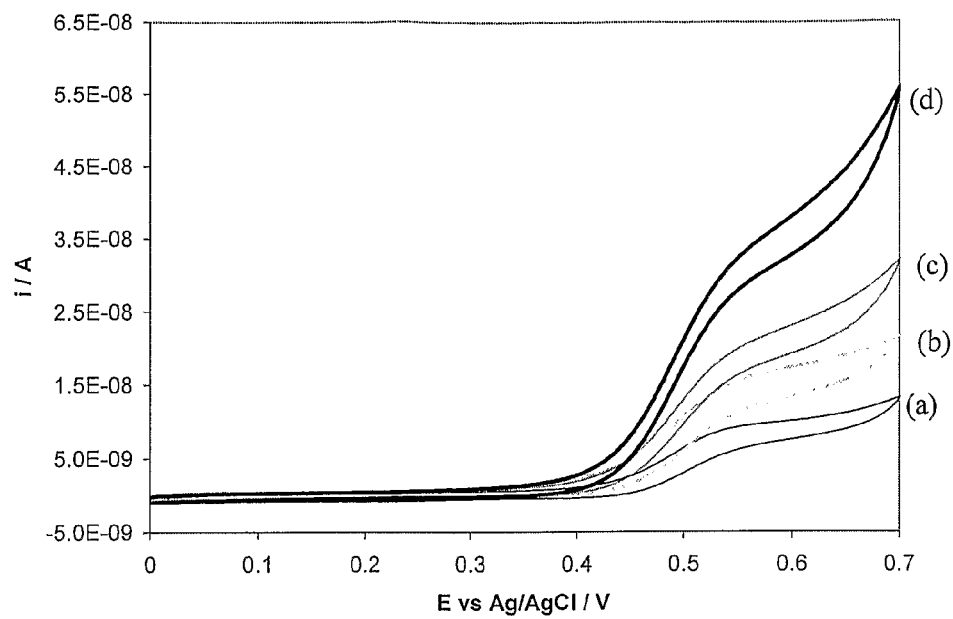
Figure 32:
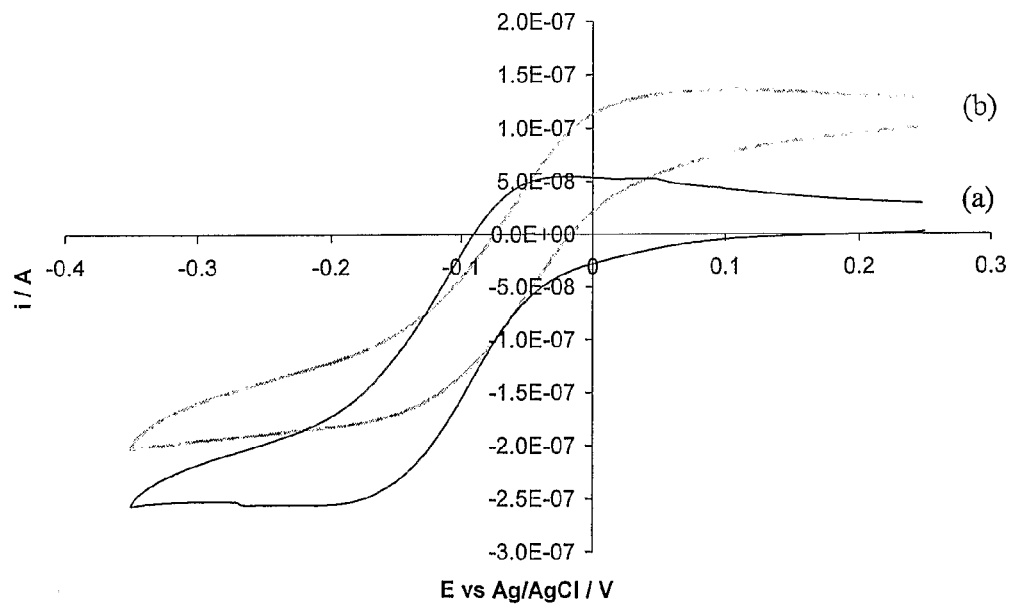
Figure 33:
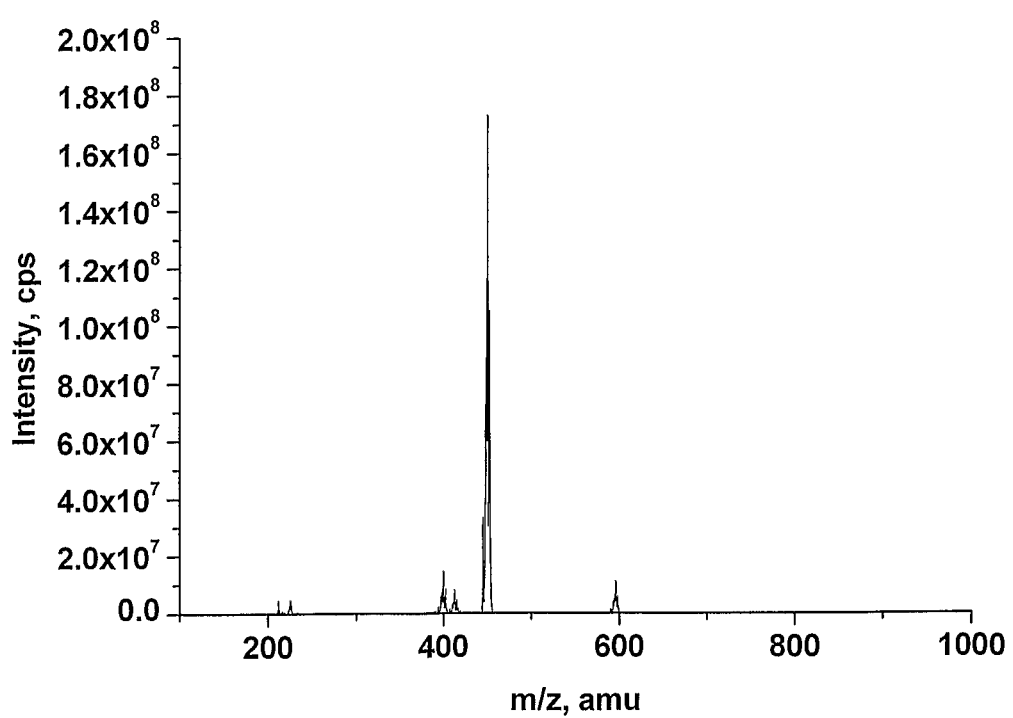
Figure 34:
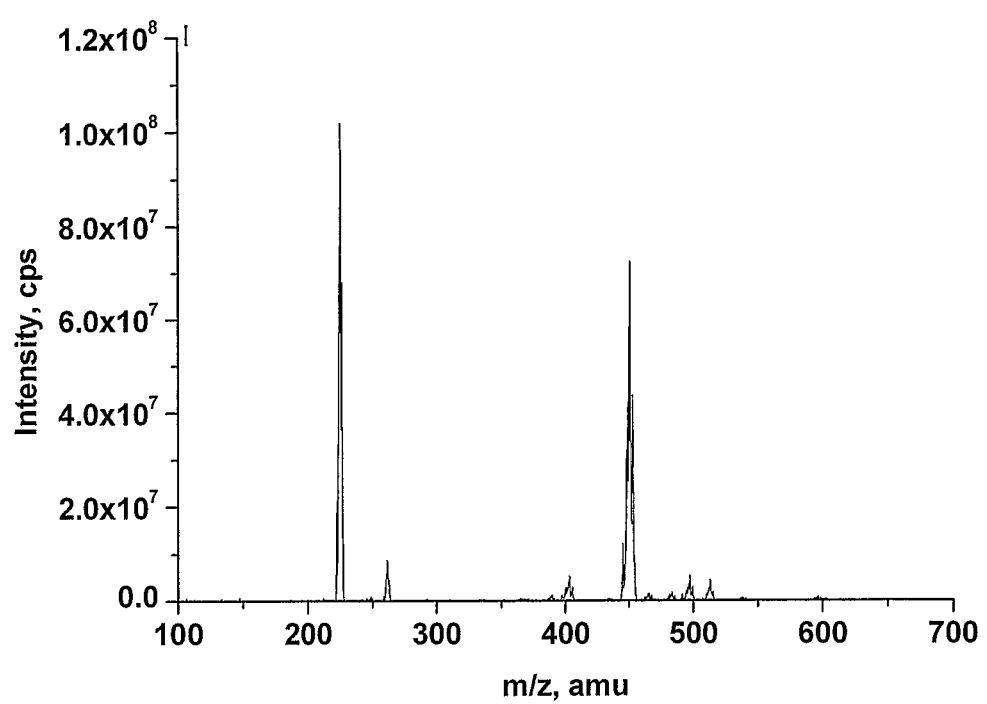
Figure 35:
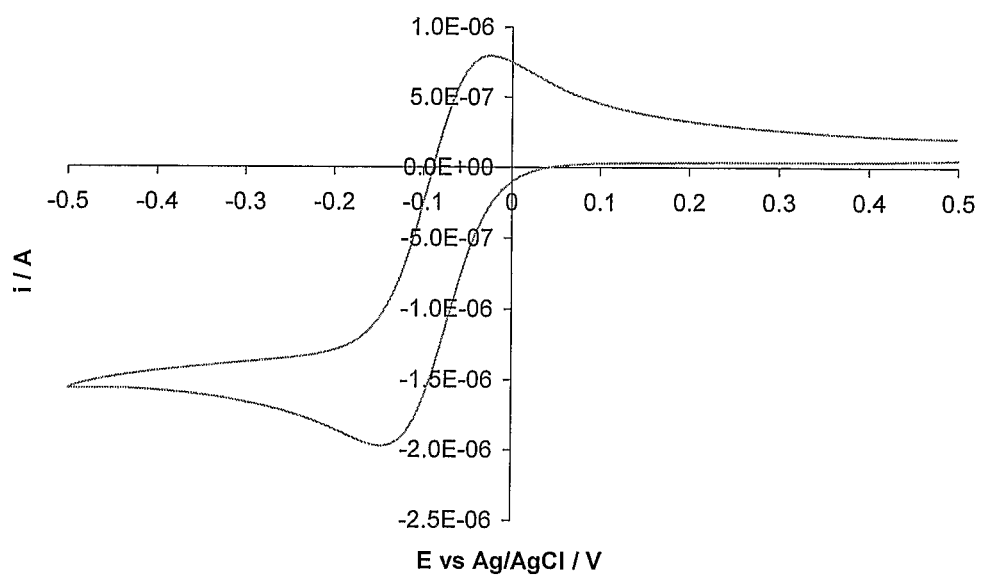
Figure 36:
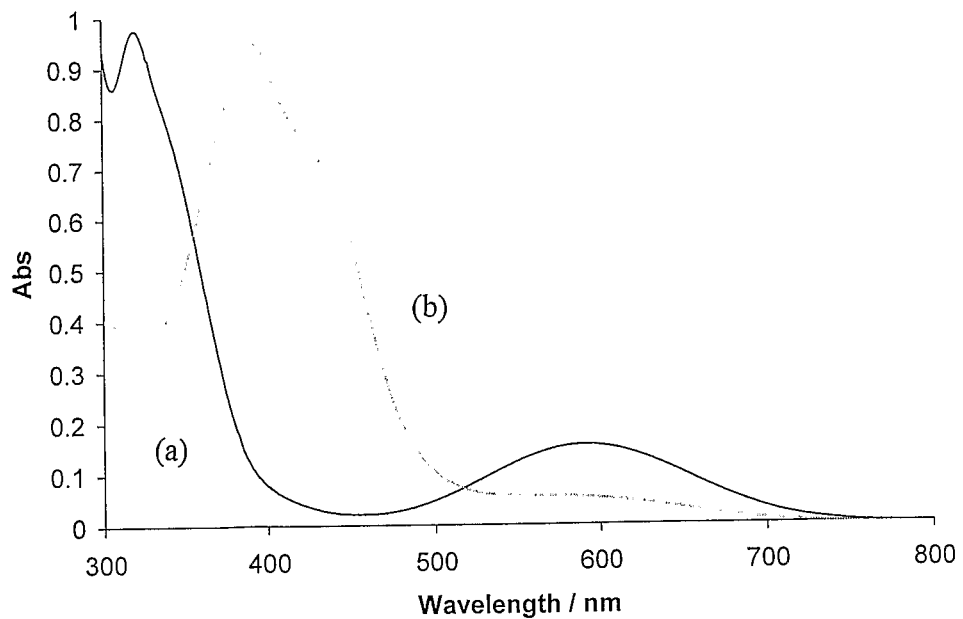
Figure 37:
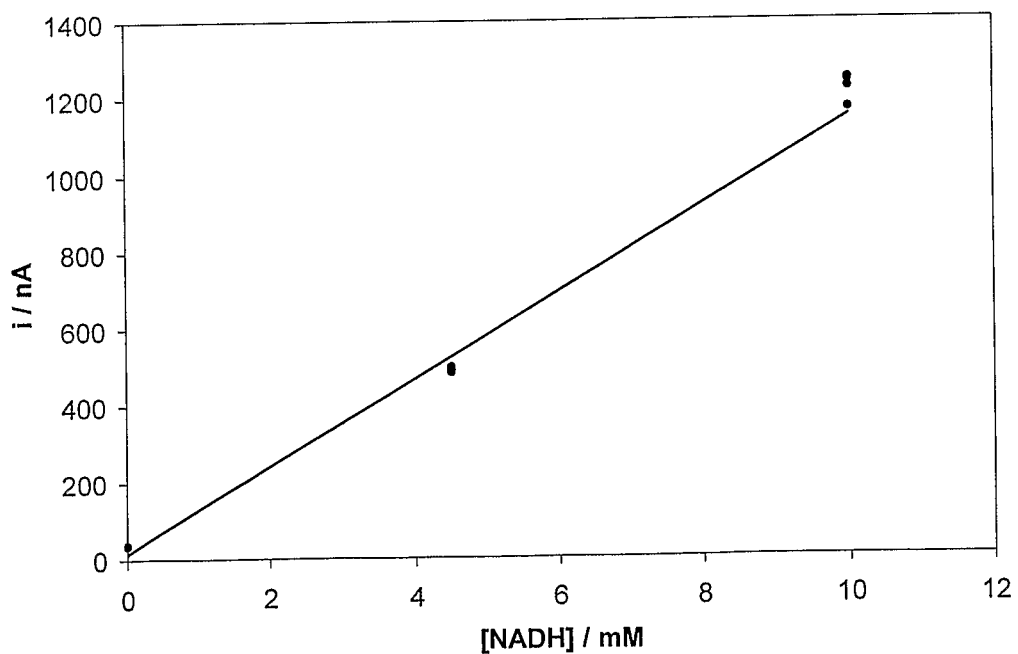
Figure 38:
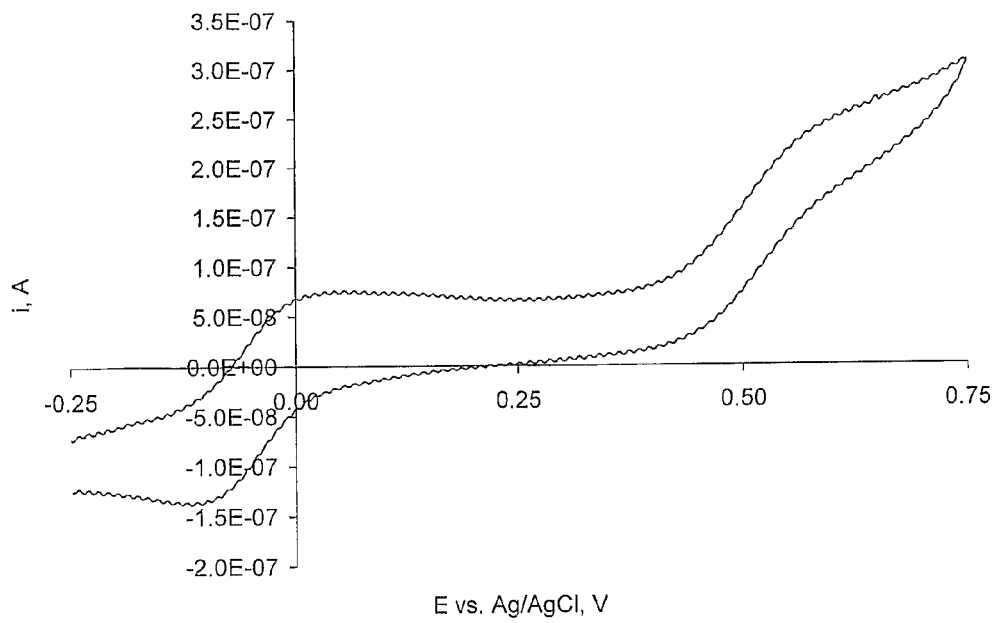

FIG. 28 shows a cyclic voltammogram (at 10 mV s$^{-1}$) of [Os$^{II}$(2,2'-bpy)$_2$(acac)]Cl (1 mM) in a 0.1M Tris (pH9.0) on a screen printed carbon micro-electrode strip, containing (a) 0, (b) 0.1, (c) 0.5, (d) 1 and (e) 5 mg ml$^{-1}$ PdR in the presence of 10 mM NADH FIG. 29 shows cyclic voltammograms for a screen printed carbon micro-electrode strip in a solution containing 1 mM [Ru$^{II}$(2,2'-bpy)$_2$(acac)]Cl, 0.1 M KCl, 16 mM Chaps and 0.1 M Tris buffer (pH9.0) recorded with a scan rate of 10 mV·s$^{-1}$;

FIG. 30 shows cyclic voltammograms (at 10 mV·s$^{-1}$) of [Ru(2,2'-bpy)$_2$(acac)]Cl (1 mM) in a 0.1 M Tris (pH7.0) on a screen printed carbon micro-electrode strip, containing (a) 0, (b) 0.5, (c) 1.25 and (d) 2.5 mg·ml$^{-1}$ glucose oxidase in the presence of 0.1 M glucose;

FIG. 31 shows cyclic voltammograms (at 10 mV·s$^{-1}$) of [Ru$^{II}$(2,2'-bpy)$_2$(C$_2$O$_4$)] (1 mM) in a 0.1 M Tris (pH7.0) on a screen printed carbon micro-electrode strip, containing (a) 0, (b) 0.25, (c) 1.25, and (d) 5 mg ml$^{-1}$ glucose oxidase in the presence of 0.1 M glucose;

FIG. 32 shows cyclic voltammograms (at 100 mV·s$^{-1}$) of K[Ru$^{III}$(C$_2$O$_4$)$_2$(py-3-COOH)$_2$] (5 mM) in 0.1 M Tris (pH7.0) on a screen printed carbon micro-electrode strip, containing (a) 0 and (b) 5 mg ml$^{-1}$ glucose oxidase in the presence of 0.1 M glucose;

FIG. 33 shows an ESI mass spectrum (+ve mode) of [Ru$^{II}$(Me$_3$TACN)(acac)(py)]PF$_6$ in CH$_3$CN;

FIG. 34 shows an ESI mass spectrum (+ve mode) of [Ru$^{III}$(Me$_3$-TACN)(acac)(py)](NO$_3$)$_2$ in methanol;

FIG. 35 shows a cyclic voltammogram for a screen printed carbon micro-electrode strip in a solution containing 10 mM [Ru$^{III}$(Me$_3$-TACN)(acac)(py)](NO$_3$)$_2$, 0.1 M KCl and 0.1 M Tris buffer (pH9.0) recorded with a scan rate of 100 mV·s$^{-1}$;

FIG. 36 shows the UV-Vis absorbption spectrum of a solution containing 2 mM [Ru$^{III}$(Me$_3$-TACN)(acac)(py)](NO$_3$)$_2$ and 5 mM NADH in the absence (dark—(a)) and presence (light—(b)) of 0.033 mg·ml$^{-1}$ PdR;

FIG. 37 shows a plot of oxidation current versus NADH concentration for a 10 mM [Ru$^{III}$(Me$_3$-TACN)(acac)(py)](NO$_3$)$_2$ solution containing 1 mg ml$^{-1}$ PdR;

FIG. 38 shows a cyclic voltammogram for a screen printed carbon micro-electrode strip in a solution containing 3.3 mM [Ru$^{III}$(acac)$_2$(2,2'-bpy-4,4'-(COOH)(COO)], 0.1 M KCl, and 0.1 M Tris buffer (pH9.0) recorded with a scan rate of 100 mV·s$^{-1}$.

Figure 39:
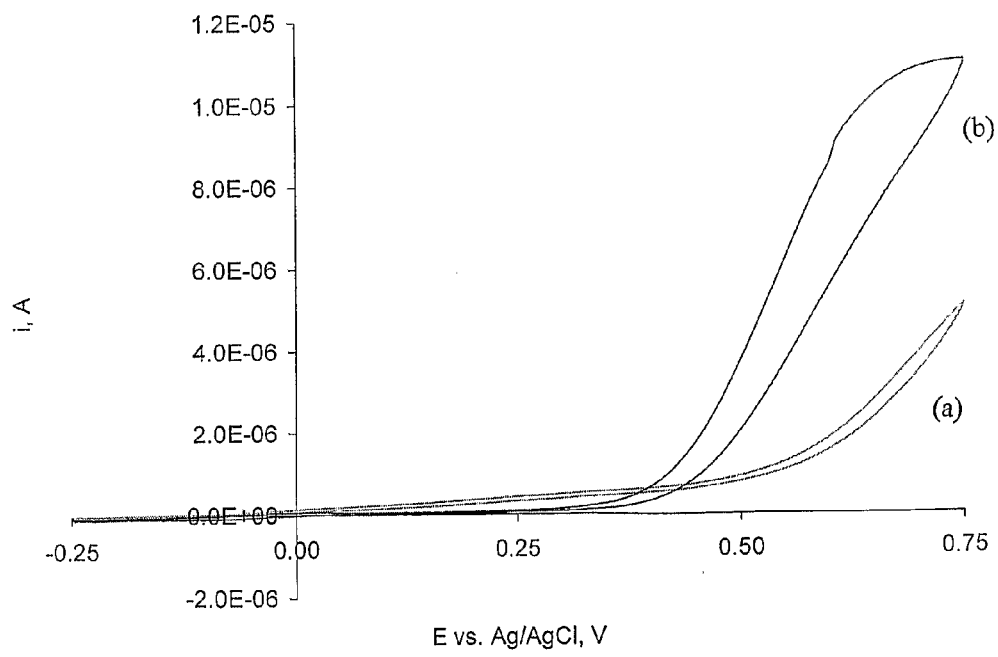

FIG. 39 shows cyclic voltammograms (at 100 mV s$^{-1}$) of [Ru$^{III}$(acac)$_2$(2,2'-bpy-4,4'-(COOH)(COO)] (3.3 mM) in a solution containing 0.1 M KCl, and 0.1 M Tris buffer (pH9.0) on a standard screen printed carbon micro-electrode strip, containing (a) 0, and (b) 10 mg·ml$^{-1}$ PdR in the presence of 50 mM NADH.

Figure 40:

FIG. 40 shows the reduced (left) and oxidized (right) forms of 10 mM solutions of the mediators of the present invention in 0.1 M KCl; and FIG. 41 shows examples of ruthenium complexes in accordance with the present invention.

All solutions were prepared using either Milli-Q reagent water from a Millipore Synergy 185 water purification system or reagent grade solvents. All solids were used as received without further purification. The mediators were tested for mediation using either enzyme mediation or using an enzyme cascade. The electrode and formulations for the enzyme cascade are described in our co-pending application WO200356319.

The following mediators were synthesised:
[Ru$^{III}$(NH$_3$)$_5$(py-3-COOH)](PF$_6$)$_2$(CF$_3$SO$_3$); [Ru$^{III}$(acac)$_2$(py-3-COOH)(py-3-COO)]; [Ru$^{III}$(3-Bracac)$_2$(py-3-COOH)(py-3-COO)]; [Ru$^{III}$(acac)$_2$(2,2'-bpy-5,5'-(COOH)(COO)]; [Ru$^{III}$(acac)$_2$(2,2'-bpy-4,4'-(COOH)(COO)]; [Ru$^{III}$(acac)$_2$(2,2'-bpy)]Cl; [Ru$^{III}$(acac)$_2$(py-4-COOH)(py-4-COO)]; [Ru$^{III}$(5-Cl-Quin)$_2$(py-3-COOH)(py-3-COO)]; [Ru$^{III}$(Me$_6$-tet)(acac)](PF$_6$)(CF$_3$SO$_3$); [Ru$^{III}$(Me$_6$-tet)(acac)]Cl$_2$; [Os$^{II}$(2,2'-bpy)$_2$(acac)]Cl; [Ru(2,2'-bpy)$_2$(acac)]Cl; [Ru$^{III}$(2,2'-bpy)$_2$(C$_2$O$_4$)]; K[Ru$^{III}$(C$_2$O$_4$)$_2$(py-3-COOH)$_2$]; and [Ru$^{III}$(Me$_3$-TACN)(acac)(py)](NO$_3$)$_2$ where py=pyridine; 3-Bracac=3-bromo-2,4-pentandionate; acac=2,4-pentandionate; 2,2'-bpy=2,2'bipyridine; 2,2'-bpy-5,5'-(COOH)$_2$=2,2'-bipyridine-5,5'-dicarboxylic acid; Me$_6$-tet=1,1,4,7,10,10-hexamethyltriethylenetetramine; Me$_3$-TACN=1,4,7-trimethyl-1,4,7-triazacyclononane, and 5-Cl-Quin=5-chloro-8-hydroxyquinoline.

For each of the complexes specifically the corresponding ruthenium or osmium complex can be prepared following the same synthetic procedure and simply changing the starting compound to the corresponding ruthenium or osmium compound.

Synthesis of [Ru$^{II}$(NH$_3$)$_5$(py-3-CO$_2$H)](PF$_6$)$_2$ and [Ru$^{III}$(NH$_3$)$_5$(py-3-CO$_2$H)](PF$_6$)$_2$(CF$_3$SO$_3$)

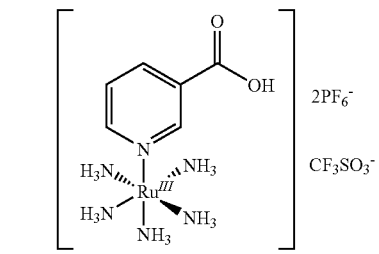

Materials
RuCl$_3$.3H$_2$O (Heraeus)
Hydrazine monohydrate (80%, RDH)
Nicotinic Acid (Aldrich)
Silver p-toluene sulfonate (Aldrich)
Silver trifluoromethanesulfonate (Aldrich)
Ammonium hexafluorophosphate (Aldrich)
Chloropentaamineruthenium(III) chloride, [Ru(NH$_3$)$_5$Cl]Cl$_2$, was prepared according to a literature method (A. D.

Allen, *Inorg. Synth.* 1970, 12, 2) from ruthenium trichloride and was purified by recrystallization from 0.1 M HCl at 40° C.

[Ru$^{II}$(NH$_3$)$_5$(py-3-CO$_2$H)](PF$_6$)$_2$

To a suspension of [Ru(NH$_3$)$_5$Cl]Cl$_2$ (1.0 g, 3.4 mmol) in 40 mL water was added two equivalent of silver p-toluene sulfonate (1.9 g, 6.8 mmol). After stirring the mixture for 1 h at room temperature, the solution was filtered to remove AgCl. To the resulting light yellow solution, which had been degassed with argon, four-fold excess of nicotinic acid (py-3-CO$_2$H, 1.67 g, 13.6 mmol) and 12-15 pieces mossy zinc amalgam (ca. 10 g) were added. After stirring the mixture for 2 hr at room temperature under Ar, the solution was filtered. To the resulting reddish orange solution, excess ammonium hexafluorophosphate (NH$_4$PF$_6$, 3 g) was added and the mixture was left at 4° C. overnight. After filtration and recrystallization of this crude product from acetone-diethyl ether, 0.6 g of [Ru$^{II}$(NH$_3$)$_5$(py-3-CO$_2$H)](PF$_6$)$_2$ was obtained. (Yield: 29.5%)

[Ru$^{III}$(NH$_3$)$_5$(py-3-CO$_2$H)](PF$_6$)$_2$(CF$_3$SO$_3$)

To a solution of [Ru$^{II}$(NH$_3$)$_5$(py-3-CO$_2$H)](PF$_6$)$_2$ (160 mg, 0.27 mmol) in 30 mL acetone, 1.3 equivalent of silver trifluoromethanesulfonate (AgCF$_3$SO$_3$, 89 mg) was added and the mixture was stirred in the dark for 1 h at room temperature. The silver was removed by centrifugation to give a light yellow solution. The resulting solution was added dropwise with stirring to 250 ml diethyl ether and the mixture was left at 4° C. for 3 h to obtain a light yellow precipitate. The product was washed with diethyl ether and recrystallized from acetone and diethyl ether. (Yield: 90 mg, 44%).

Synthesis of cis-[Ru$^{II}$(acac)$_2$(py-3-COOH)$_2$]

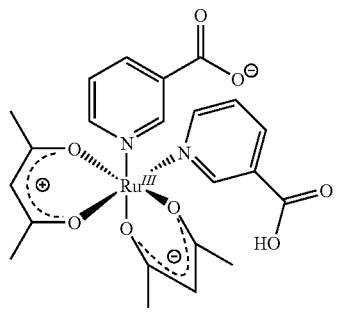

A mixture of Ru(acac)$_3$ (200 mg, 0.5 mmol) and nicotinic acid (494 mg, 4 mmol) in ethanol was refluxed under argon with several pieces of mossy zinc amalgam for 5 h. The resulting brownish red mixture was cooled and the Zn/Hg removed by filtration. The brownish red precipitate was collected by filtration and washed with 0.1M HCl, water and diethyl ether. (Crude product yield: 250 mg, 91% containing Zn/Hg debris).

Synthesis of cis-[Ru$^{III}$(acac)$_2$(py-3-COOH)(py-3-COO)]

cis-[Ru$^{II}$(acac)$_2$(py-3-COOH)$_2$] (200 mg) was dissolved in 0.1 M NH$_3$ and then filtered. The reddish brown filtrate was stirred in air overnight (ca. 18 hours) to give a dark purple solution. The solution was filtered and evaporated to dryness. The dark purple residue was collected and washed with acetone and diethyl ether, and then air dried. (Yield: 150 mg.)

Synthesis of cis-[Ru$^{III}$(3-Bracac)$_2$(py-3-COO)(py-3-COOH)]

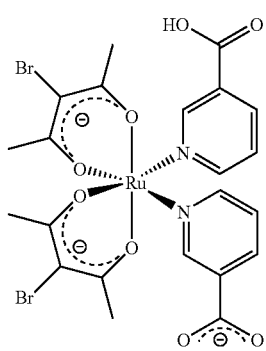

cis-[Ru$^{III}$(acac)$_2$(py-3-COO)(py-3-COOH)] (93 mg, 0.17 mmol) was dissolved in 2 ml H$_2$O. 4.3 ml of 0.041 M bromine water (0.17 mmol of Br$_2$) was then added. The resulting purplish blue suspension was stirred in air overnight. The blue precipitate was collected and washed with water. Yield=25%; E°=0.15 V vs NHE at pH=8 (phosphate buffer).

Synthesis of [Ru$^{III}$(acac)$_2$(5,5'-(COO)(COOH)-2,2'-bpy)]

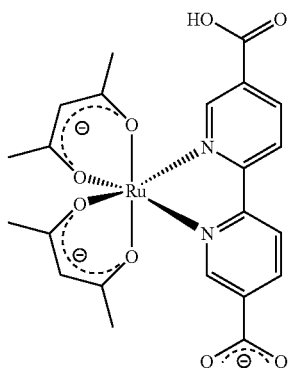

A red mixture of Ru(acac)$_3$ (200 mg, 0.5 mmol) and 5,5'-(COOH)$_2$-2,2'-bpy (122 mg, 0.5 mmol) in 30 ml ethanol was refluxed under argon with several pieces of mossy Zn/Hg amalgam overnight. The resulting brown mixture was cooled and the zinc amalgam was removed with tweezers. The brown precipitate was collected and washed with ethanol and diethyl ether. The brown solid was then dissolved in 50 ml 0.1 M NH$_3$ and filtered. The green filtrate was stirred in air overnight to give a red solution. The solution was filtered and then evaporated to dryness. The purple-red precipitate was collected and washed with acetone and diethyl ether and then air dried. Yield: 22%; E°=0.18 V vs NHE at pH=8 (phosphate buffer)

15

[Ru$^{III}$(acac)$_2$(2,2'-bpy)](PF$_6$)

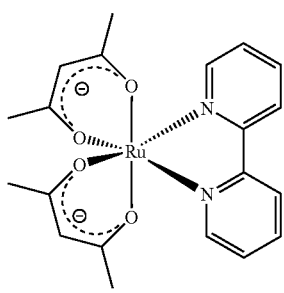

[Ru$^{II}$(acac)$_2$(2,2'-bpy)] (75 mg, 0.165 mmol) was dissolved in dichloromethane (15 ml). A solution of ferrocenium hexafluorophosphate (54.6 mg, 0.165 mmol) in dichloromethane (10 ml) was added in small portions to the solution of [Ru$^{II}$(acac)$_2$(2,2'-bpy)] with vigorous stirring at room temperature. The color of the solution turned from deep green to reddish after a few minutes. After stirring for ten more minutes, the solution was filtered and diethyl ether (60 ml) was added and the precipitate was collected by centrifugation and washed with diethyl ether. (Yield=50%)

Synthesis of [Ru$^{III}$(acac)$_2$(2,2'-bpy)]Cl

A solution of [Bu$_4$N]Cl (463 mg, 1.667 mmol) in acetone (15 ml) was added dropwise to a solution of [Ru$^{III}$(acac)$_2$(2,2'-bpy)](PF$_6$) (200 mg, 0.333 mmol) in 20 ml acetone with stirring at room temperature. The purple precipitate was collected by filtration, washed with acetone and diethyl ether and then air dried. The precipitate was re-dissolved in acetonitrile and purified by crystallisation via vapour diffusion with diethyl ether. (Yield=50%)

Synthesis of [Ru$^{II}$(acac)$_2$(py-4-COOH)$_2$]

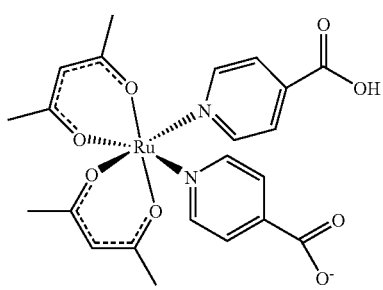

A red mixture of Ru(acac)$_3$ (200 mg, 0.5 mmol) and py-4-COOH (124 mg, 1 mmol) in 40 ml ethanol was refluxed under argon with several pieces of mossy Zn/Hg amalgam for 4 hours. The resulting deep purple mixture was cooled and the zinc amalgam was removed with tweezers. The dark brown precipitate was collected by filtration and washed with 0.1 M HCl, water and then diethyl ether. (Yield of crude product=250 mg, 91%, contains Zn amalgam)

Synthesis of [Ru$^{III}$(acac)$_2$(py-4-COOH)(py-4-COO)]

Ru$^{II}$(acac)$_2$(py-4-COOH)$_2$ (250 mg) was dissolved in 0.1 M NH$_3$ and then filtered. The reddish brown filtrate was stirred in air overnight to give a purple solution. The solution was filtered and then evaporated to dryness. The purple precipitate was collected, washed with acetone and diethyl ether and then air dried. Yield=50%; E°=0.12 V vs NHE at pH=8 (phosphate buffer)

16

Synthesis of [Ru$^{III}$(5-Cl-Quin)$_2$(py-3-COOH)(py-3-COO)]

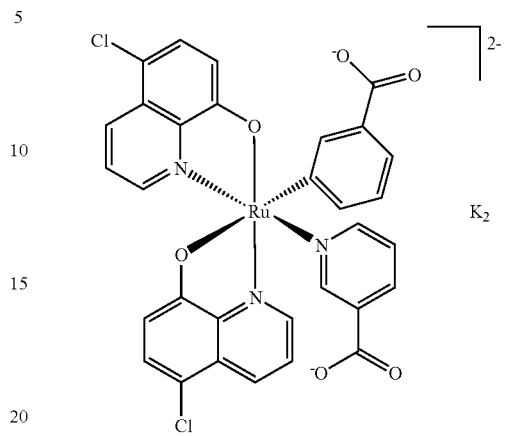

Chemical Formula: C$_{30}$H$_{18}$Cl$_2$K$_2$N$_4$O$_6$Ru$^{2-}$
Exact Mass: 779.89

A solution of nicotinic acid (92.3 mg, 0.75 mmol) and Ru(5-Cl-Quin)$_3$ (200 mg, 0.37 mmol) in ethanol (25 ml) was refluxed under argon with several pieces of zinc amalgam for 24 h. The resulting light brown solid was isolated by filtration, washed with ethanol and air dried. The brown solid was suspended in water (15 ml) and KOH (0.2 g, 3.57 mmol) was added. After stirring for 0.5 h, the resulting dark brown solution was filtered and rota-evaporated to dryness. The residue was washed with ethanol and recrystallized by dissolving in 1:1 methanol/ethanol and then slowly evaporating the solution to around ca. 50% of its original volume. The solid was dried in vacuo at 60° C. Yield: 57% (150 mg, 0.21 mmol). MS: m/z 634 (M+1). E°=0.097 V vs NHE at pH=8 (phosphate buffer).

Synthesis of [Ru$^{II}$(Tet-Me$_6$)(acac)](PF6)

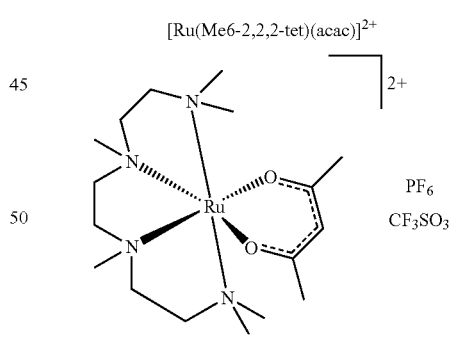

Chemical Formula: C$_{18}$H$_{37}$F$_9$N$_4$O$_5$PRuS
Molecular Weight: 724.60
Elemental Analysis: C, 29.84; H, 5.15; F, 23.60;
N, 7.73; O, 11.04; P, 4.27; Ru, 13.95; S, 4.43

A yellow mixture of cis-[Ru$^{III}$(Tet-Me$_6$)Cl$_2$](PF$_6$) (100 mg, 0.18 mmol) and Li(acac) (40 mg, 0.36 mmol) in 10 ml ethanol was refluxed overnight. The resulting brown solution was cooled and then filtered. The filtrate was concentrated to ca. 1 ml, diethyl ether was added and the brown precipitate was filtered, washed with diethyl ether and then air dried. Yield=85%. Calcd. for RuC$_{17}$H$_{37}$N$_4$O$_2$PF$_6$: C, 35.48%; H, 6.48%; N, 9.73%. Found C, 35.39%; H, 6.37%; N, 9.60%

Synthesis of [Ru$^{III}$(Tet-Me$_6$)(acac)](PF$_6$)(CF$_3$SO$_3$)

AgCF$_3$SO$_3$ (67 mg, 0.26 mmol) was added to a solution of [Ru$^{II}$(Tet-Me$_6$)(acac)](PF$_6$) (125 mg, 0.22 mmol) in 10 ml acetone. The brown solution turned blue immediately and the mixture was stirred in the dark for 30 min. The silver metal in the solution was removed by centrifugation and the blue solution was then slowly added to ca. 80 ml diethyl ether. The blue precipitate was collected by filtration, washed with diethyl ether and then dried in vacuo overnight. Yield=70%; E°=0.18 V vs NHE at pH=8 (phosphate buffer).

Synthesis of [Ru$^{III}$(Tet-Me$_6$)(acac)]Cl$_2$

Addition of [n-Bu$_4$N]Cl to a solution of [Ru(Me$_6$-tet)(acac)](PF$_6$)(CF$_3$SO$_3$) in MeOH resulted in a precipitate of [Ru(Me$_6$-tet)(acac)]Cl$_2$, which was filtered and dried in vacuo overnight.

Synthesis of [Os$^{II}$(acac)(bipy)$_2$]Cl

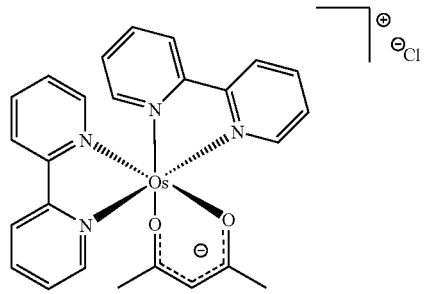

Acetylacetone (1 ml) was added to [Os$^{II}$(bipy)$_2$Cl$_2$] (0.25 g, 0.44 mmol) in water (20 ml) and alcohol (10 ml), and the mixture refluxed for 6 h in the presence of excess CaCO$_3$ (0.5 g). The volatiles were evaporated off and the residue was extracted with chloroform (30 ml). The intensely red-brown chloroform extract was filtered and dried with anhydrous Na$_2$SO$_4$, evaporated to a small volume and on addition of diethyl ether, [Os$^{II}$(bpy)$_2$(acac)Cl] crystallized as dark orange-brown platelets. These were then filtered and air-dried. Yield: 63% (0.176 g, 0.28 mmol). MS: m/z 603 (M). E°=0.31 V vs NHE at pH=8 (phosphate buffer).

Synthesis of [Ru$^{II}$(bipy)$_2$(acac)]Cl

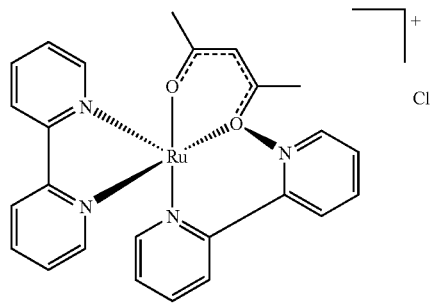

Chemical Formula: C$_{25}$H$_{23}$ClN$_4$O$_2$Ru
Exact Mass: 548.06

Acetylacetone (1 ml, 9.70 mmol) was added to [Ru(bipy)$_2$Cl$_2$] (300 mg, 0.62 mmol) suspended in water (20 ml) and ethanol (20 ml), and the mixture was refluxed for 6 hr in the presence of excess CaCO$_3$. The mixture was filtered and filtrate was rota-evaporatred to dryness. The residue was extracted with chloroform (30 ml) and filtered. The filtrate was dried over MgSO$_4$ and then evaporated to approx. 5 ml. On addition of diethyl ether, [Ru$^{II}$(bipy)$_2$(acac)]Cl crystallized slowly as a dark brown crystalline solid. The solid was dried in vacuo at 60° C. Yield: 70% (236 mg, 0.43 mmol). MS: m/z 513 (M). E°=0.71V vs NHE at pH=8 (phosphate buffer).

Synthesis of Ru$^{II}$(bipy)$_2$ox

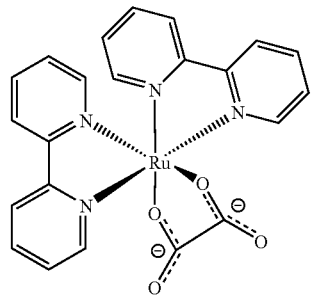

Ru(bipy)$_2$Cl$_2$ (0.2 g, 0.41 mmol) was suspended in water (20 ml) and ethanol (10 ml) and the mixture was boiled for 2 min. Potassium oxalate dihydrate (52.1 mg, 0.41 mmol) was added and the mixture was heated under reflux for 2 h to give a bright red solution. On cooling a green crystalline solid was obtained, which was filtered, washed with water and diethyl ether and air-dried. Yield: 94%, 0.19 g. MS: m/z 503.1 (M). E°=32.5 mV vs Fc/Fc$^+$ in 0.1 M TBHP in acetonitrile.

Synthesis of K[Ru$^{III}$(ox)$_2$(py-3-COOH)$_2$]

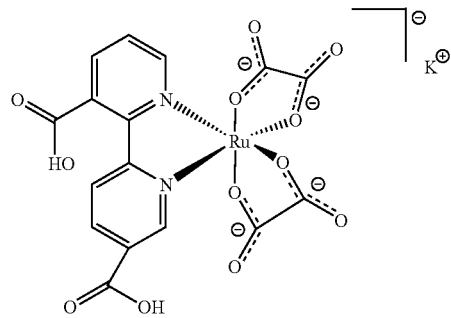

A solution of K$_3$[Ru(ox)$_3$] (500 mg, 1.0 mmol) and py-3-COOH (255 mg, 2.1 mmol) in 50 ml H$_2$O was refluxed in air overnight. The resulting brown solution was cooled and then filtered. The filtrate was concentrated to ca. 1 ml, acetone was added and the pale brown precipitate was filtered and washed with acetone and diethyl ether. The crude product was recrystallized three times from H$_2$O/acetone. Yield: 70%. ESI-MS: m/z=602 (M+K)$^+$. E$_{1/2}$ of Ru$^{III/II}$=0.16 V vs. NHE in phosphate buffer solution (pH 8.05).

Preparation of [Ru$^{II}$(DMSO)$_4$Cl$_2$]

Ruthenium trichloride trihydrate (1.0 g) was refluxed in dimethyl sulphoxide (5 mL) for 5 min. The volume was reduced to half in vacuo, addition of acetone (20 mL) gave a yellow precipitate. The yellow complex which separated was filtered off, washed with acetone and ether, and vacuum dried.

Preparation of [Ru$^{III}$(L)Cl$_3$]

To a mixture of Ru$^{II}$(DMSO)$_4$Cl$_2$ (1.0 g, 2.1 mmol) in absolute ethanol (25 mL) was added L (0.80 g, 4.7 mmol) (L=1,4,7-trimethyl-1,4,7-triazacyclononane) with stirring. The suspension was heated to 60° C. for 1 h until a clear deep red-brown solution was obtained, which was then refluxed for 2 h. The solvent was removed under reduced pressure by rotary evaporation. The red-orange residue was treated with concentrated HCl and heated under reflux for 30 min in the presence of air. An orange microcrystalline solid was collected by filtration, washed with water, ethanol and diethyl ether, and air-dried.

Preparation of [Ru$^{III}$(L)(acac)(OH)]PF$_6$.H$_2$O

Solid Ru$^{III}$(L)Cl$_3$ (2.0 g; 5.0 mmol) was added in small amounts to a solution of sodium 2,4-pentanedionate (acac) (3.0 g; ~24 mmol) in water (60 mL) with stirring at ambient temperature. The mixture was stirred for 3.5 h until a clear red solution was obtained. Addition of a solution of NaPF$_6$ (2.0 g) in H$_2$O (5 mL) and cooling to 0° C. initiated the precipitation of orange microcrystals, which were collected by filtration, washed with diethyl ether, and air-dried.

Preparation of [Ru$^{II}$(L)(acac)(py)]PF$_6$

A solution containing [Ru$^{III}$(L)(acac)(OH)]PF$_6$ (105 mg, 0.20 mmol) in absolute ethanol/pyridine (5 mL) (4:1, v/v) was heated to reflux under argon atmosphere in the presence of 10 pieces of Zn amalgram for 4 h. After cooling to ambient temperature, the red microcrystalline precipitate was collected by filtration, washed with diethyl ether, and air-dried. The product was recrystallized from acetone/diethyl ether. Yield: (94 mg, 79%) ESI/MS (positive mode): m/z=451, [M]$^+$. E$_{1/2}$ of Ru$^{III/II}$=−0.18 V vs. Fc$^{+/0}$ in 0.1 M TBAH in CH$_3$CN.

Preparation of [Ru$^{III}$(L)(acac)(py)](NO$_3$)$_2$

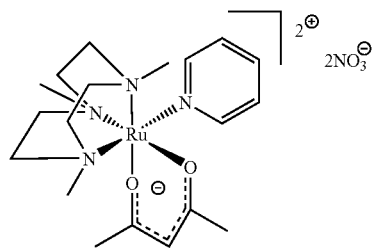

A solution of AgCF$_3$SO$_3$ (42 mg, 0.16 mmol) in acetone (1 mL) was slowly added to an orange acetone solution (3 mL) containing [Ru$^{II}$(Me$_3$-TACN)(acac)(py)]PF$_6$ (90 mg, 0.15 mmol). After stirring for 5 min., solid [n-Bu$_4$N]NO$_3$ (304 mg, 1 mmol) was added, and the purple precipitate was filtered, washed with acetone and then diethyl ether. The product was recrystallized from methanol/diethyl ether. Yield: (64 mg, 87%) ESI/MS (positive mode): m/z=451.0, [M]$^+$; 225.4, [M]$^{2+}$. E° of Ru$^{III/II}$=0.2 V vs. NHE in pH8.05 phosphate buffer.

Synthesis of [Ru$^{III}$(acac)$_2$(4,4'-(COO)(COOH)-2,2'-bpy)]

A red mixture of Ru(acac)$_3$ (200 mg, 0.5 mmol) and 4,4'-(COOH)$_2$-2,2'-bpy (122 mg, 0.5 mmol) in 30 ml ethanol was refluxed under argon with several pieces of mossy Zn/Hg amalgam overnight. The resulting brown mixture was cooled and the zinc amalgam was removed with tweezers. The brown precipitate was collected and washed with ethanol and diethyl ether. The brown solid was then dissolved in 50 ml 0.1 M NH$_3$, filtered and stirred in air overnight to give a purple-red solution. The solution was filtered and then evaporated to dryness. The purple precipitate was collected and washed with acetone and diethyl ether and then air dried. Yield: 45%. E°=0.21 V vs. NHE at pH=8 (phosphate buffer).

Electrochemical Tests

Testing Mediation Using Cyclic Voltammetry (PdR)

In order to test the mediators which were synthesized in the reduced form, i.e. [Ru$^{III}$(5-Cl-Quin)$_2$(py-3-COOH)(py-3-COO)] and [Os$^{II}$(2,2'-bpy)$_2$(acac)]Cl, a set of experiments were undertaken where the Ru$^{2+}$ (Ru$^{II}$(5-Cl-Quin)$_2$(py-3-COOH)(py-3-COO) or Os$^{2+}$ ([Os$^{II}$(2,2'-bpy)$_2$(acac)]Cl) were electrochemically oxidized in the presence of NADH. Addition of putdaredoxin reductase (PdR) (mediating enzyme) resulted in electrocatalysis, identified by a large increase in the oxidation current and the absence of a reduction peak in the reverse scan.

Solution Preparation for Testing Mediation Using Cyclic Voltammetry (PdR)

A series of putdaredoxin reductase (Biocatalysts Ltd., Wales) solutions were made by dissolving PdR in Trizma® Pre-set crystals pH9 made up to 0.1 M (Sigma-Aldrich Company Ltd) to obtain a 10 mg/mL stock solution which was sequentially diluted to obtain solutions with different PdR concentrations. These solutions were then mixed 1:1 (v:v) with either NADH (Sigma-Aldrich Company Ltd.) or TNADH (Oriental Yeast Company, Japan) solution containing the mediator. All final solutions tested had 1 mM mediator, 5 mM TNADH (or 10 mM NADH) and varying concentrations of PdR (5 mg ml$^{-1}$ to 0.1 mg ml$^{-1}$).

Solution preparation for Testing Mediation Using Cyclic Voltammetry (GOx)

A series of glucose oxidase (GOx) (Sigma-Aldrich Company Ltd.) solutions were made by dissolving GOx in Trizma® Pre-set crystals pH7 made up to 0.1 M (Sigma-Aldrich Company Ltd.) to obtain a 10 mg/mL stock solution which was sequentially diluted to obtain solutions with different GOx concentration. These solutions were then mixed 1:1 (v:v) with either NADH (Sigma-Aldrich Company Ltd) or TNADH (Oriental Yeast Company, Japan.) solution containing mediator. All final solutions tested had 1 mM mediator, 5 mM TNADH (or 10 mM NADH) and varying concentrations of GOx (2.5 mg ml$^{-1}$ to 0.5 mg ml$^{-1}$).

Experiment 1

In order to determine the electrochemical response of the new mediator [Ru(II)(py-3-COOH)(NH$_3$)$_5$](PF$_6$)$_2$, the 10 mM mediator solution (prepared using non-deoxygenated water) was placed onto a standard electrode and tested using cyclic voltammetry.

Figure 1:
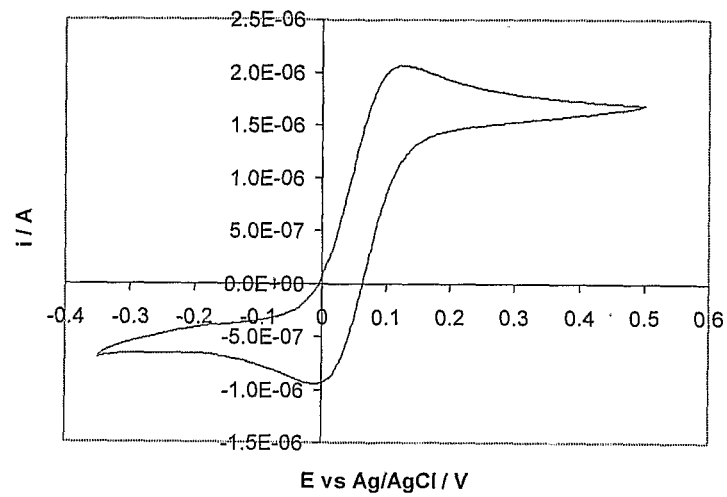
FIG. 1 shows the voltammetry of a 10 mM solution of mediator [Ru$^{II}$(py-$_3$COOH)(NH$_3$)$_5$](PF$_6$)$_2$ in 0.1 M KCl in buffer recorded using the standard well electrodes as described in WO200356319 with a scan rate of 100 mVs$^{-1}$.

The results are shown in FIG. 1 which is a cyclic voltammogram of 10 mM mediator solution (oxygenated) tested on a standard electrode, cycling between −0.35 V and 0.5 V at a scan rate of 100 mV·s$^{-1}$. The voltammogram shows clearly defined peaks for the oxidation and subsequent reduction of the mediator, with a relatively small peak separation.

Experiment 2

In order to test the stability of the reduced form of the new mediator [Ru$^{II}$(py-3-COOH)(NH$_3$)$_5$](PF$_6$)$_2$ to direct oxidation by dissolved oxygen, the sensors were tested by repeated oxidation in both anaerobic and aerobic conditions (using the same solutions).

Figure 2:
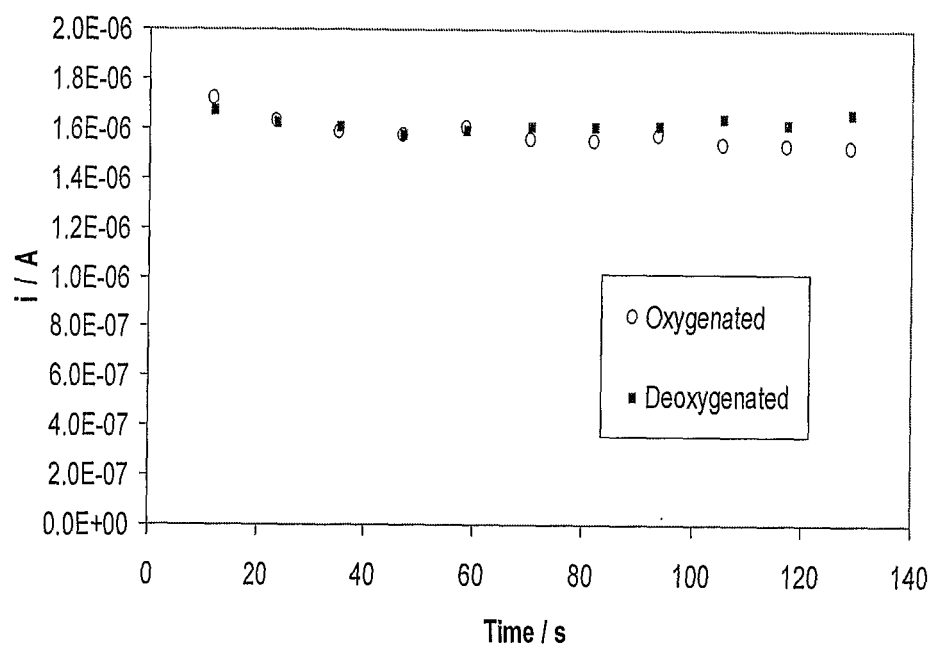
FIG. 2 shows repeat oxidative testing (at +0.25 V vs Ag/AgCl) of 10 mM new mediator [(Ru$^{II}$(py-$_3$COOH)(NH$_3$)$_5$](PF$_6$)$_2$ in 0.1 M KCl recorded in deoxygenated (red) and oxygenated (blue) environments.

FIG. 2 shows the repeat oxidation (at +0.25 V vs Ag/AgCl) results obtained when the sensors were tested in the glove box (squares) and in open air (circles).

The results showed that the oxidation current of the new mediator decreased with repeat testing—circa 12% with 11 repeat oxidations—but the effect of dissolved oxygen is significantly reduced when compared to Ru(NH$_3$)$_6$Cl$_2$.

Experiment 3

The voltammetry of the mediator [Ru$^{II}$(py-3-COOH)(NH$_3$)$_5$](PF$_6$)$_2$) was investigated under the conditions described in Experiment 1 in 0.1 M pH9 Tris to determine whether it remained the same. Cyclic voltammetry was performed using a 100 mV sec$^{-1}$ sweep rate, starting at 0 V, sweeping in the positive direction initially with sweep limits of +0.5 V and −0.35 V vs. Ag/AgCl. FIG. 3 shows voltammograms of the mediator in water (containing 0.1 M KCl) and in 0.1 M Tris, pH9. The voltammograms were very similar with similar peak potentials and absolute currents. The smaller peak for the reduction of the Ru$^{3+}$ species compared to the oxidation of the Ru$^{2+}$ species indicated that the species in solution was predominantly Ru$^{2+}$. Similar experiments undertaken with the Ru(NH$_3$)$_6$Cl$_2$ gsve a 50:50 ratio of peak currents for the Ru$^{2+}$/Ru$_{3+}$ redox couple.

Experiment 4

The stability of the mediator [Ru$^{II}$(py-3-COOH)(NH$_3$)$_5$](PF$_6$)$_2$ to oxidation by oxygen was studied on standard electrodes. Solutions of 10, 5 and 1 mM of the new mediator in 1% sodium taurocholate (NaTC), 50 mM MgSO$_4$, 0.1 M KCl in 0.1 M Tris buffer, pH9, were prepared and then tested on standard electrodes using the repeat time protocol with a potential of +0.25 V vs Ag/AgCl. The results are shown in FIG. 4. The data show that the new mediator is stable to oxidation by oxygen at all mediator concentrations tested. The calibration plot for the new mediator gives a gradient of 156 nA/mM, compared to 199 nA/mM for the standard ruthenium hexamine mediator (recorded for the same sheet of electrodes). The % CV (Coefficient of Variance) from the plot (2.84%) was almost identical to that observed for the standard ruthenium hexamine (2.81%). The intercept for the graph is 95 nA was comparable to that observed for ruthenium hexamine (72 nA).

Experiment 5

Figure 5:
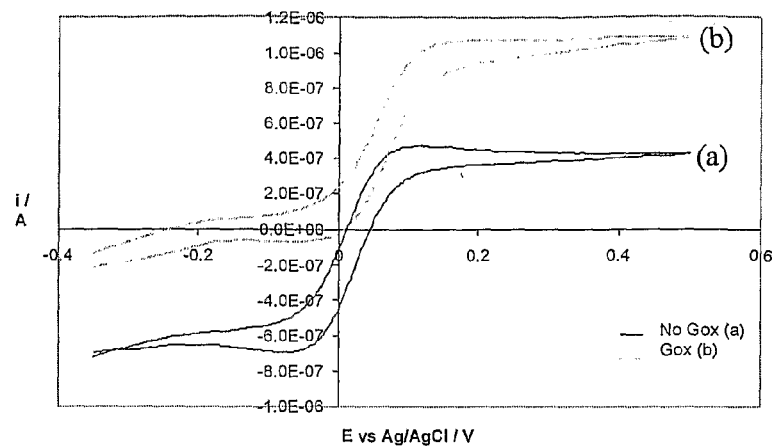
FIG. 5 shows cyclic voltammograms of [(Ru$^{II}$(py-$_3$-COOH)(NH$_3$)$_5$](PF$_6$)$_2$ in the absence (black—(a)) and presence (grey—(b)) of glucose oxidase.

To test whether the new mediator [Ru$^{II}$(py-3-COOH)(NH$_3$)$_5$](PF$_6$)$_2$ can mediate electron transfer to and from glucose oxidase (GOx), an aliquot of GOx was added to a (partially oxygen oxidized) solution of the new mediator. All other conditions were as described in Experiment 3. FIG. 5 shows the resulting voltammograms recorded in the absence and presence of GOx. The data showed that the new mediator could mediate electron transfer between GOx and an electrode.

Experiment 6

Figure 6:
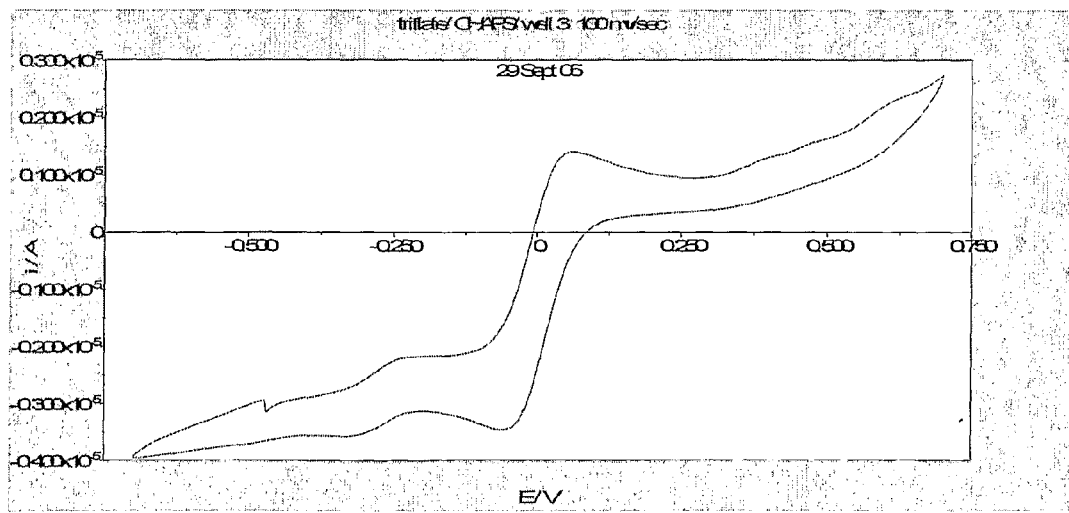
FIG. 6 shows cyclic voltammograms of [Ru$^{III}$(NH$_3$)$_5$(py-3-COOH)(PF$_6$)$_2$(CF$_3$SO$_3$), in total cholesterol mix as described in WO200356319.

The mediator, [Ru$^{III}$(NH$_3$)$_5$(py-3-COOH)](PF$_6$)$_2$(CF$_3$SO$_3$), was studied by cyclic voltammetry on bare sensors. A 50 mM solution of the mediator was prepared in 0.1 M Tris (pH9.0), 0.1 M KCl and 1% w/v surfactant (NaTC or CHAPS). The mediator dissolved readily to give solutions that were intensely yellow in colour. Cyclic voltammetry was performed using a 100 mV·sec$^{-1}$ sweep rate, starting at 0 mV, sweeping positive initially with sweep limits of +0.7 V and −0.7 V vs. Ag/AgCl. Two sweeps were performed on each well and the second sweep was saved (FIG. 6). The cyclic voltammogram was identical for each surfactant type. The voltammograms show two reduction peaks and one oxidation peak, plus a further shoulder on the oxidation wave, implying the material may contain some impurity. The oxidation potential of the peak is more positive than Ru hexamine, and a potential of +250 mV vs. Ag/AgCl was chosen for oxidative chronoamperometric experiments. The potential for reduction experiments was left unchanged at −300 mV.

Total cholesterol sensors were prepared using this mediator in 0.1 M Tris (pH9.0), 5% CHAPS, 5% deoxy bigCHAP and 66 mg/mL cholesterol dehydrogenase (ChDH). The mediator was added to give a final concentration of 48.3 mM. The sensor responses were determined using a Petex spreading membrane and 10 μl of thawed plasma.

Figure 7A:
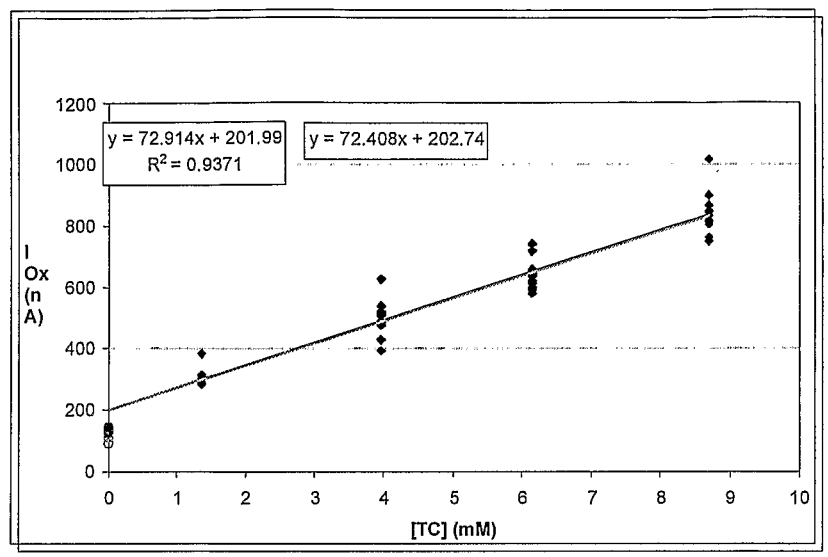
FIG. 7A shows the oxidation of total cholesterol mix with new mediator [Ru$^{III}$(NH$_3$)$_5$(py-3-COOH)](PF$_6$)$_2$(CF$_3$SO$_3$); with plasma as test solution at time=118 s.
Figure 7B:
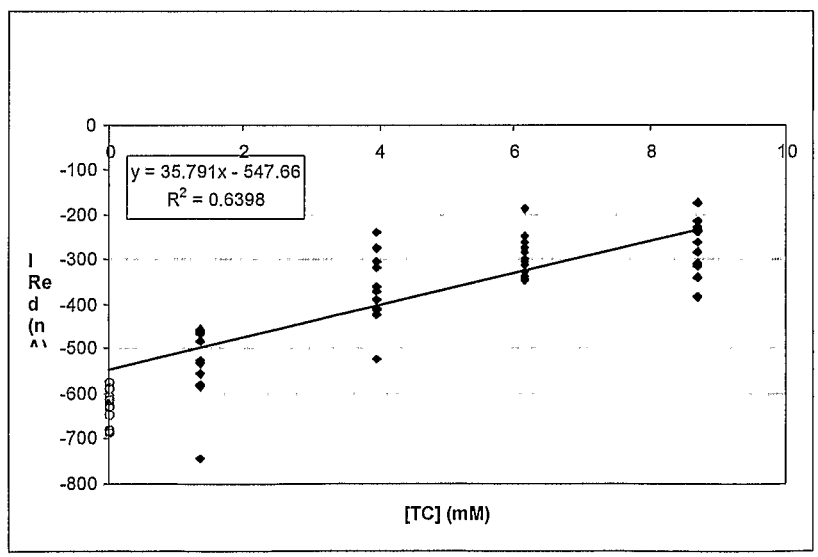
FIG. 7B shows reduction current of the total cholesterol mix with the mediator [Ru$^{III}$(NH$_3$)$_5$(py-3-COOH-pyridine)](PF$_6$)$_2$(CF$_3$SO$_3$), with plasma as test solution at time=118 s.
Figure 7C:
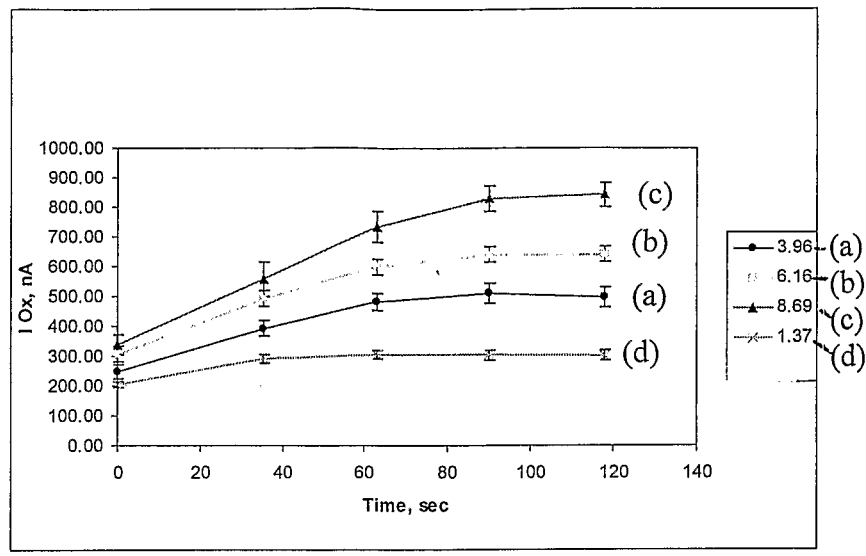
FIG. 7C shows a time point experiment with the mediator [Ru$^{III}$(NH$_3$)$_5$(3-COOH-pyridine)](PF$_6$)$_2$(CF$_3$SO$_3$), showing the change in average oxidation current over time with differing concentrations of cholesterol.
Figure 8A:
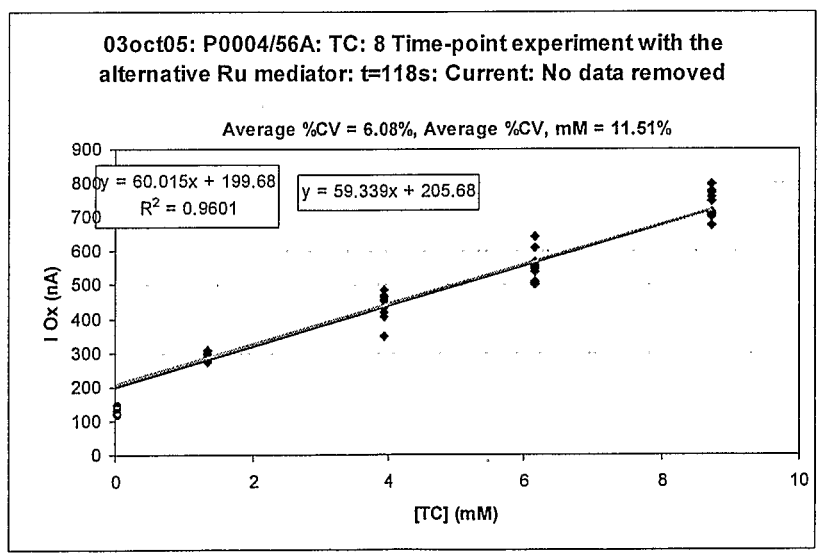
FIG. 8A shows a time point experiment of the oxidation current with the mediator [Ru$^{III}$(NH$_3$)$_5$(3-COOH-pyridine)](PF$_6$)$_2$(CF$_3$SO$_3$) at time=118 s.
Figure 8B:
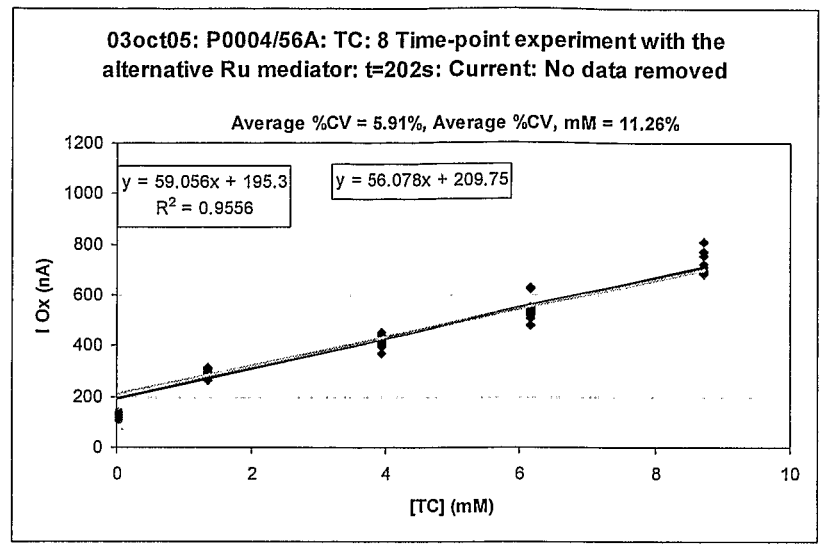
FIG. 8B shows a time point experiment of the oxidation current with the mediator [Ru$^{III}$(NH$_3$)$_5$(3-COOH-pyridine)](PF$_6$)$_2$(CF$_3$SO$_3$), at time=202 s.
Figure 8C:
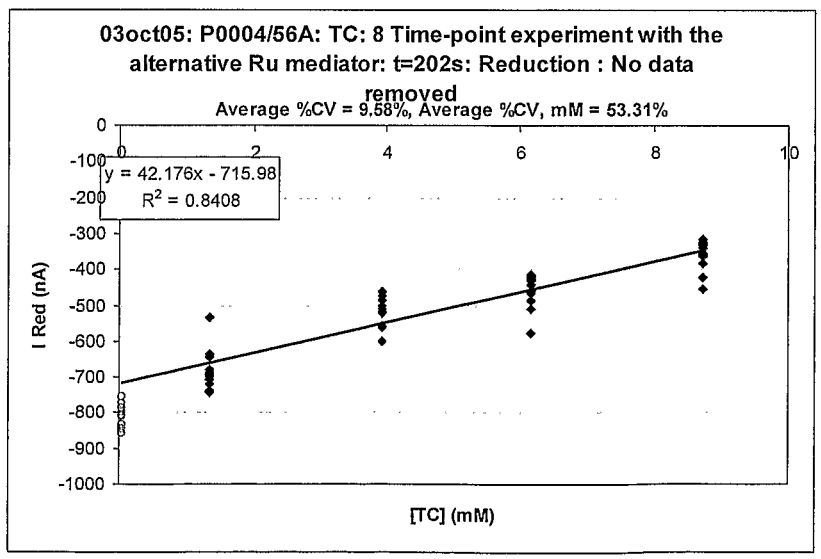
FIG. 8C shows a time point experiment of reduction current with the mediator [Ru$^{III}$(NH$_3$)$_5$(3-COOH-pyridine)](PF$_6$)$_2$(CF$_3$SO$_3$), at time=202 s.
Figure 8D:
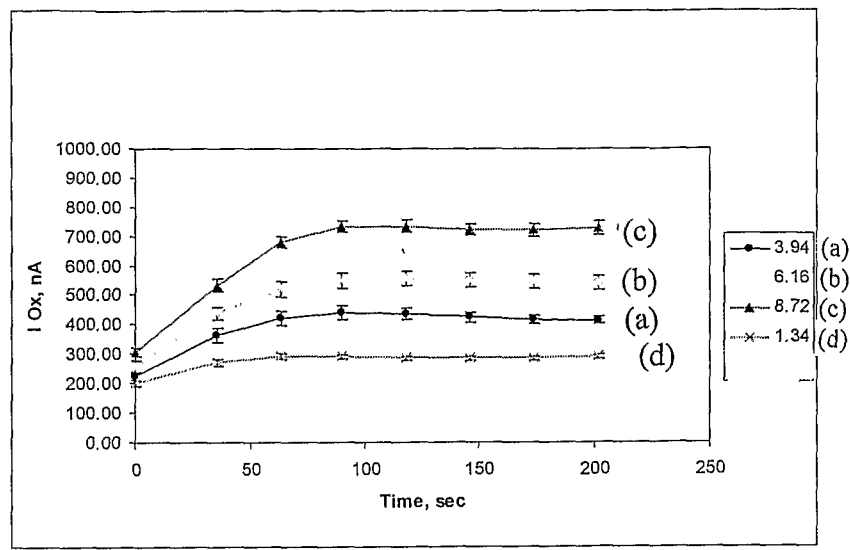
FIG. 8D shows a time point experiment with the Ru mediator [Ru(NH$_3$)$_5$(py-3-COOH)](PF$_6$)$_2$(CF$_3$SO$_3$) showing the change in average oxidation current over time with different concentrations of cholesterol.

Five repeat time measurements were performed in the first experiment. The slope of the current-concentration response was reasonably high, although the intercept was also high. This may indicate that the mediator contained some impurity (e.g. some Ru$^{II}$ species). The plot of average current vs. time (see FIGS. 7A-C) shows that the response is very stable once the maximum current value has been reached. This improved stability of response is most probably due to increased stability of the new Ru mediator. The data showed that [Ru$^{III}$(NH$_3$)$_5$(py-3-COOH)](PF$_6$)$_2$(CF$_3$SO$_3$) functioned as a mediator in the total cholesterol sensors, and that the new mediator readily underwent electron exchange with PdR.

Experiment 7

To further investigate this apparent increased stability of the new mediator [Ru$^{III}$(NH$_3$)$_5$(py-3-COOH)](PF$_6$)$_2$(CF$_3$SO$_3$) compared to the hexamine complex, a second experiment was performed using repeat time measurements for a longer time period.

The results are shown below for the sensor response at the usual measurement time (118 sec) and the final measurement time (202 sec). The responses are almost identical, indicating that the response, and hence the mediator, are very stable, in agreement with the plot of average current vs. time, also shown in FIGS. 8A to 8D.

Experiment 8

Figure 9:
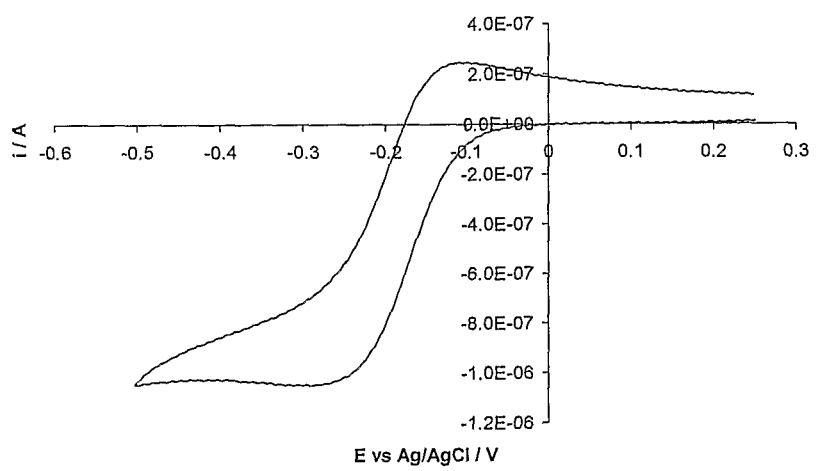
FIG. 9 shows a cyclic voltammogram for a screen printed carbon micro-electrode strip in a solution consisting of 10 mM [Ru$^{III}$(acac)$_2$(py-3-COOH)(py-3-COO)], 0.1 M KCl, 16 mM Chaps and 0.1 M Tris buffer (pH9.0) recorded with a scan rate of 100 mV·s$^{-1}$.
Figure 10:
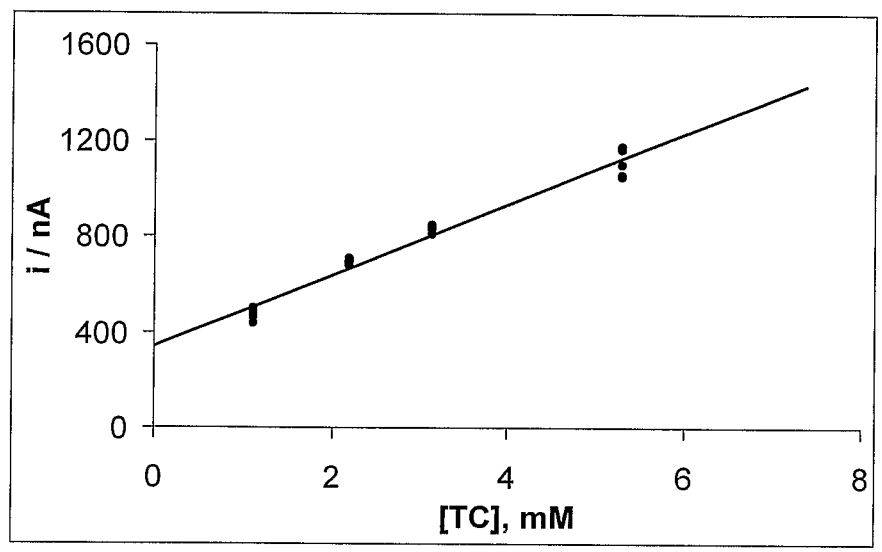
FIG. 10 shows a plot of oxidation current versus the total cholesterol (TC) concentration for different human plasma samples in wells using [Ru$^{III}$(acac)$_2$(py-3-COOH)(py-3-COO)] as the mediator. Currents were recorded after an oxidation potential of +0.15 V (vs Ag/AgCl reference) was applied to the working electrode.
Figure 11:
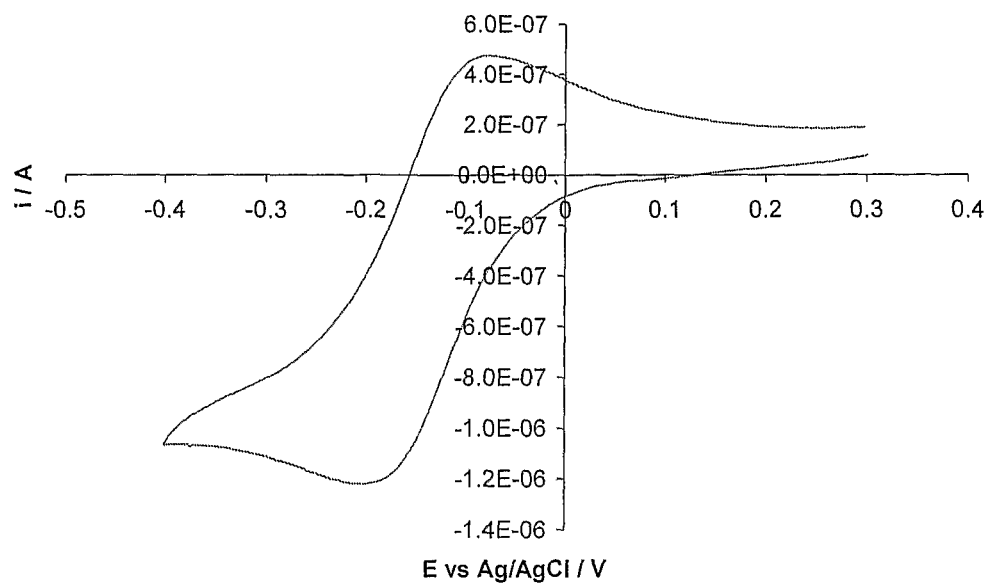
FIG. 11 shows a cyclic voltammogram for a screen printed carbon micro-electrode strip in a solution consisting of 10 mM [Ru$^{III}$(3-Bracac)$_2$(py-3-COOH)(py-3-COO)], 0.1 M KCl, 16 mM Chaps and 0.1 M TRIS buffer (pH9.0) recorded with a scan rate of 100 mV·s$^{-1}$.
Figure 12:
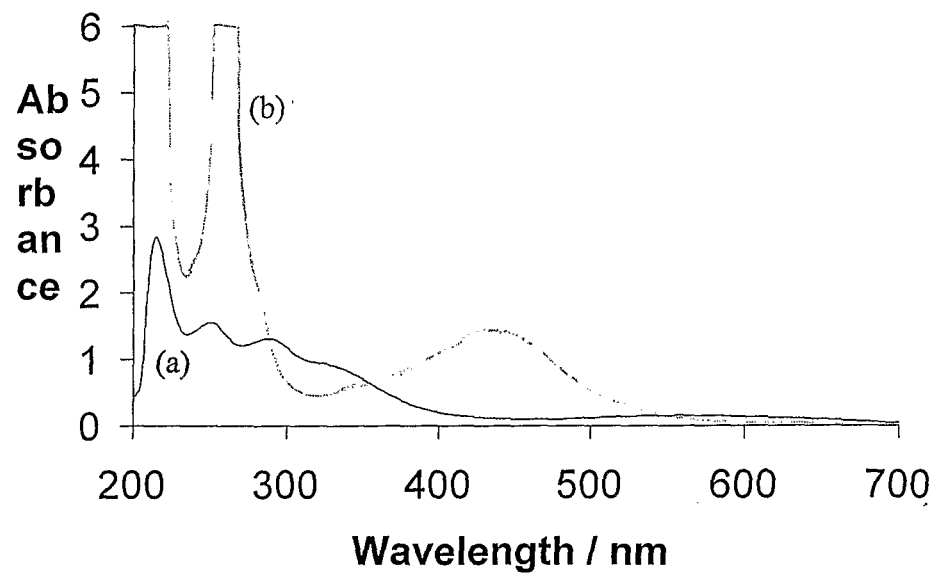
FIG. 12 shows the UV-Vis absorption spectrum of a solution consisting of 0.5 mM [Ru$^{III}$(3-Bracac)$_2$(py-3-COOH)(py-3-COO)] in the absence (black—(a)) and presence (grey—(b)) of 0.75 mM NADH and 0.03 mg ml$^{-1}$ PdR.
Figure 13:
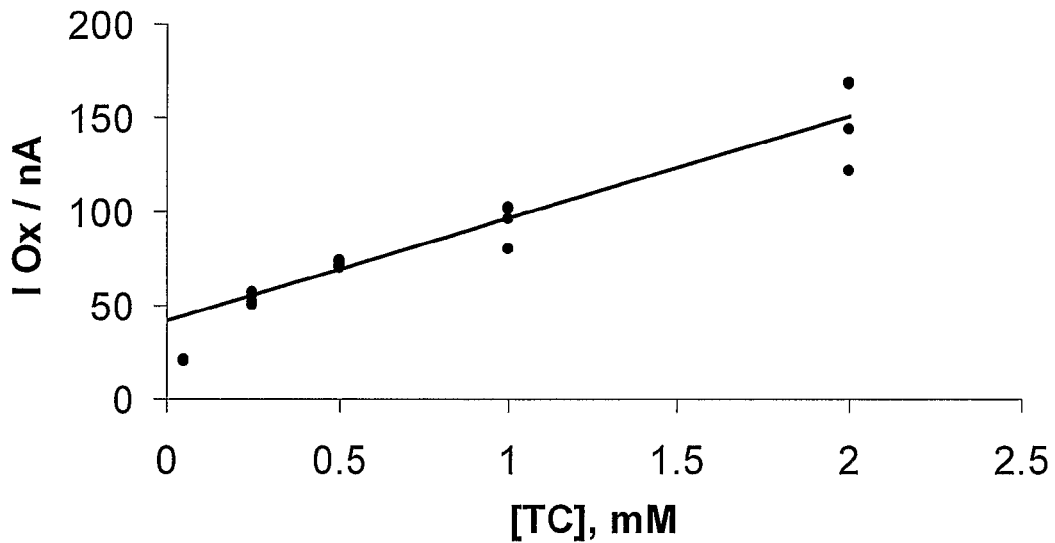
FIG. 13 shows a plot of oxidation current versus the total cholesterol (TC) concentration for different lyophilized serum samples in wells using [Ru$^{III}$(3-Bracac)$_2$(py-3-COOH)(py-3-COO)] as the mediator. Currents were recorded after an oxidation potential of +0.15 V (vs Ag/AgCl reference) was applied to the working electrode.
Figure 14:
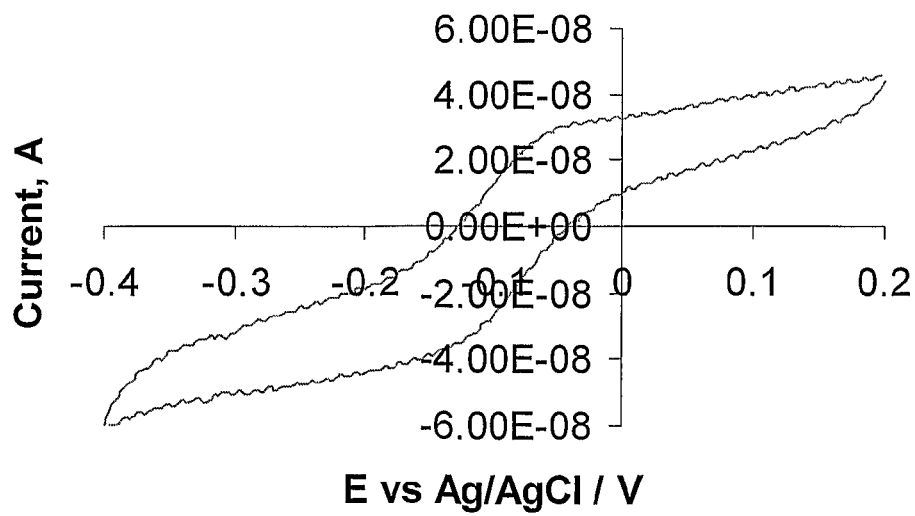
FIG. 14 shows a cyclic voltammogram for a screen printed carbon micro-electrode strip in a solution consisting of 1 mM [Ru$^{III}$(acac)$_2$(2,2'-bpy-5,5'-(COOH)(COO)], 0.1 M KCl, 16 mM Chaps and 0.1 M Tris buffer (pH9.0) recorded with a scan rate of 100 mV·s$^{-1}$.
Figure 15:
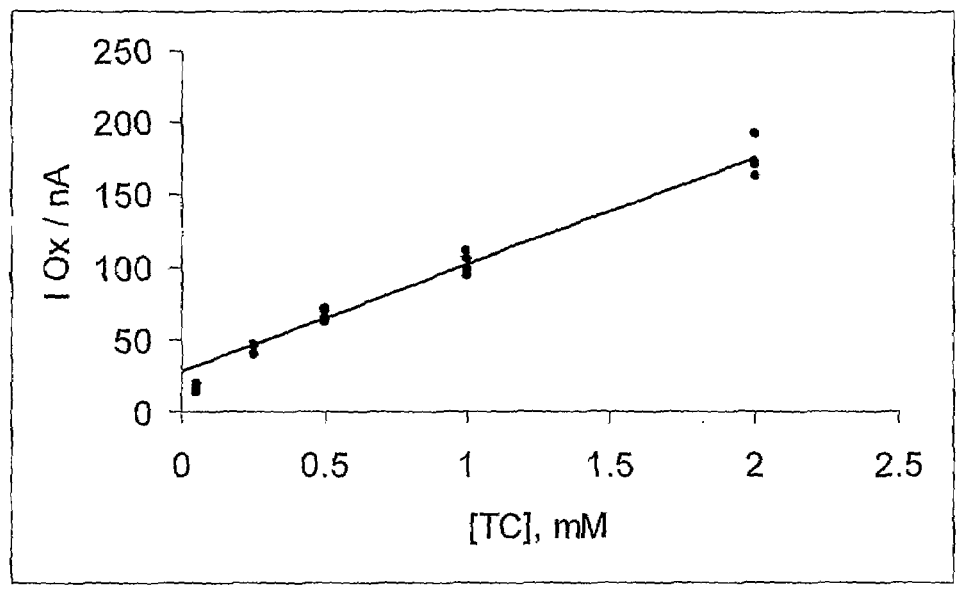
FIG. 15 shows a calibration plot of oxidation current versus the total cholesterol (TC) concentration for different lyophilized serum samples in wells using [Ru$^{III}$(acac)$_2$(2,2'-bpy-5,5'-(COOH)(COO)] as the mediator. Currents were recorded after an oxidation potential of +0.15 V (vs Ag/AgCl reference) was applied to the working electrode.
Figure 16:
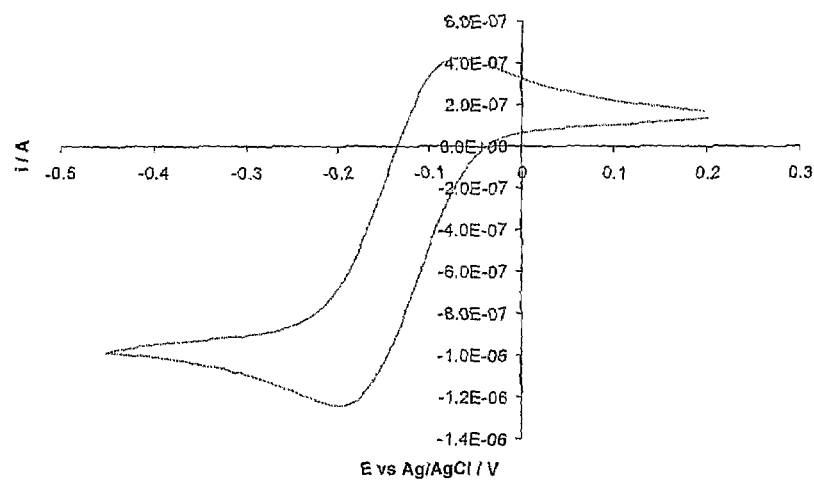
FIG. 16 shows a cyclic voltammogram for a screen printed carbon micro-electrode strip in a solution consisting of 10 mM [Ru$^{III}$(acac)$_2$(2,2'-bpy)]Cl, 0.1 M KCl, 16 mM Chaps and 0.1 M Tris buffer (pH9.0) recorded with a scan rate of 100 mV·s$^{-1}$.
Figure 17:
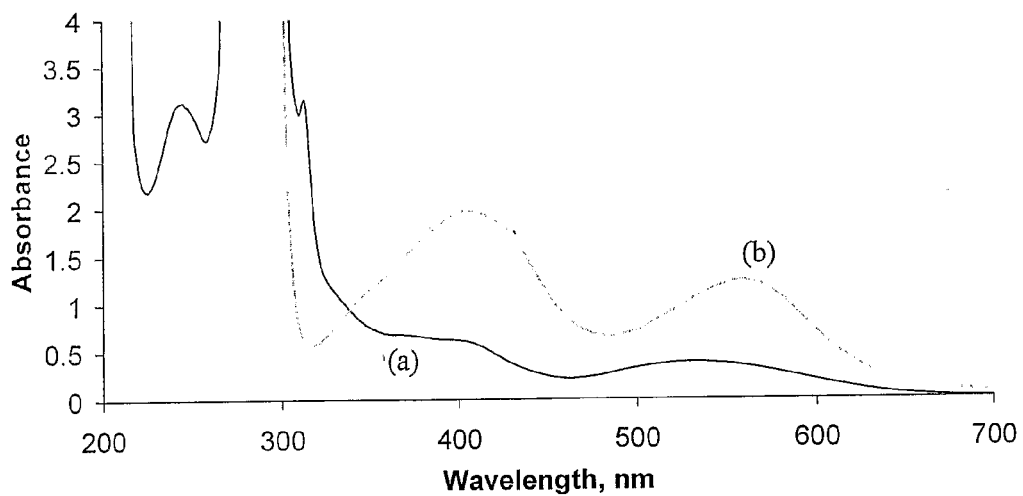
FIG. 17 shows the UV-Vis absorbption spectrum of a solution of 1 mM [Ru$^{III}$(acac)$_2$(2,2'-bpy)]Cl and 1 mM NADH in the absence (dark—(a)) and presence (light—(b)) of 0.017 mg·ml$^{-1}$ PdR.
Figure 18:
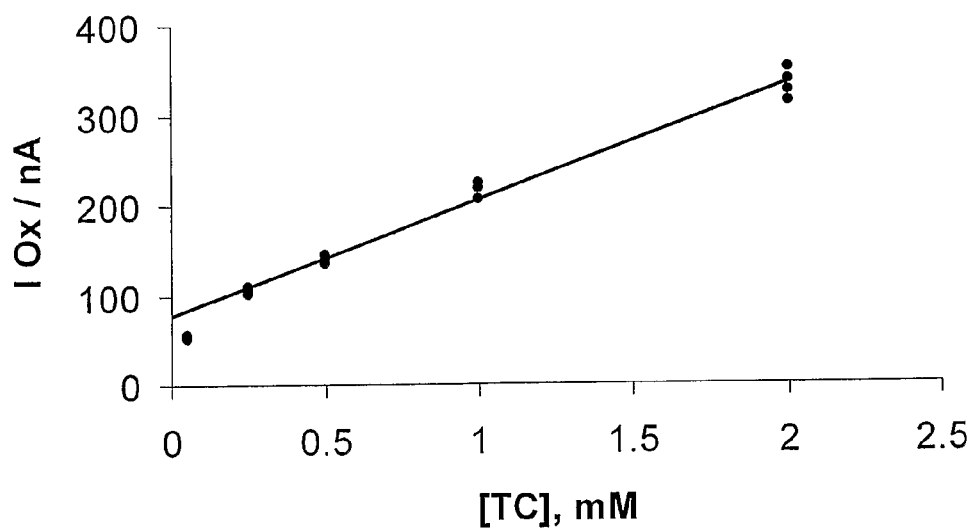
FIG. 18 shows a plot of oxidation current versus the total cholesterol (TC) concentration for different lyophilized serum samples in wells using [Ru$^{III}$(acac)$_2$(2,2'-bpy)]Cl as the mediator. Currents were recorded after an oxidation potential of +0.15 V (vs Ag/AgCl reference) was applied to the working electrode.
Figure 19:
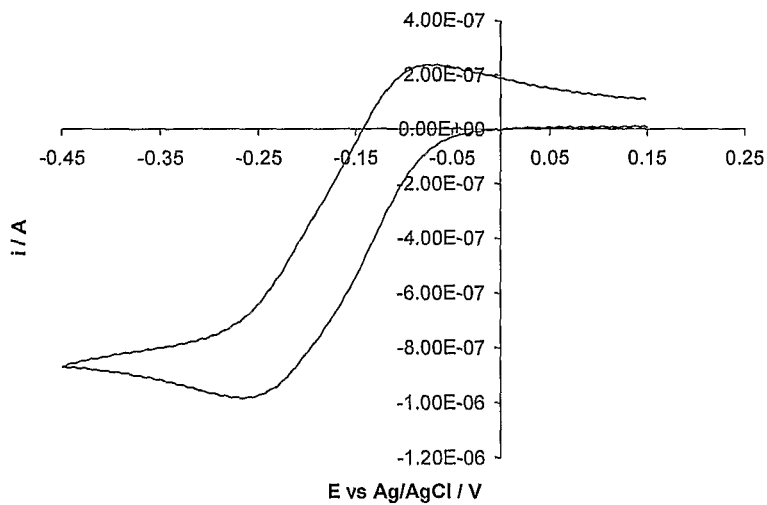
FIG. 19 shows a cyclic voltammogram for a screen printed carbon micro-electrode strip in a solution consisting of 10 mM [Ru$^{III}$(acac)$_2$(py-4-COOH)(py-4-COO)], 0.1 M KCl, 16 mM Chaps and 0.1 M Tris buffer (pH9.0) recorded with a scan rate of 100 mV·s$^{-1}$.
Figure 20:
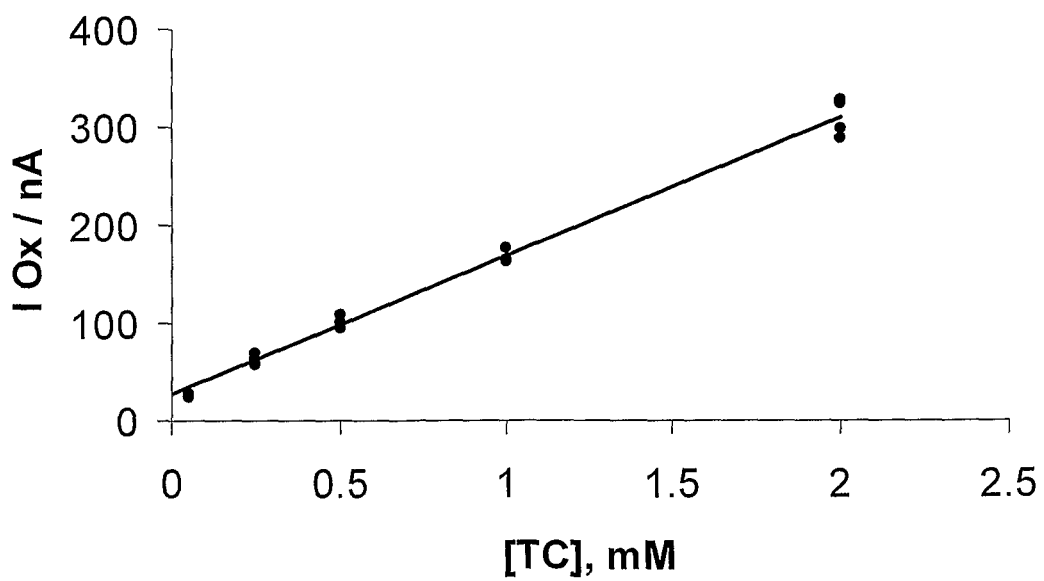
FIG. 20 shows a plot of oxidation current versus the total cholesterol (TC) concentration for different human plasma samples in wells using [Ru$^{III}$(acac)$_2$(py-4-COOH)(py-4-COO)] as the mediator. Currents were recorded after an oxidation potential of +0.15 V (vs Ag/AgCl reference) was applied.
Figure 21:
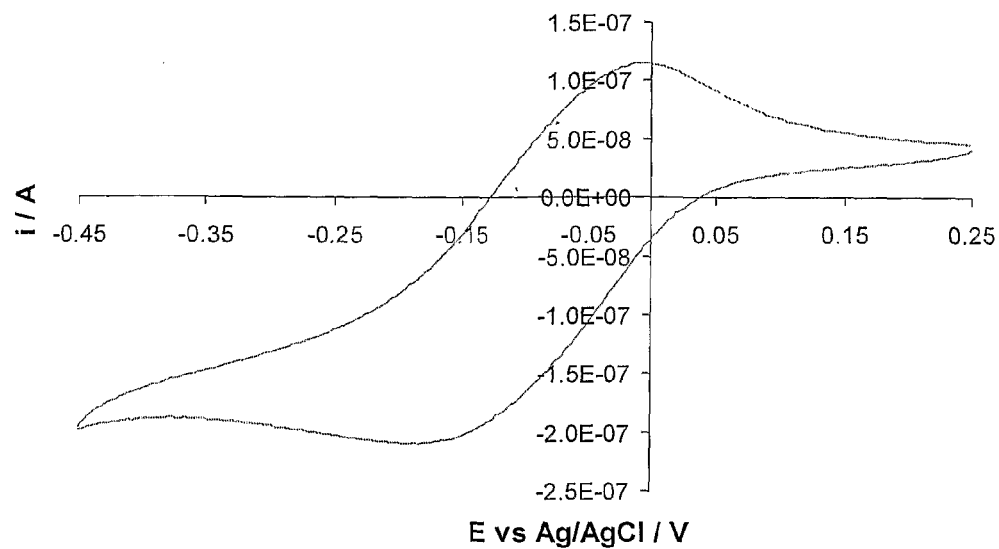
FIG. 21 shows a cyclic voltammogram for a screen printed carbon micro-electrode strip in a solution consisting of 10 mM [Ru$^{III}$(5-Cl-Quin)$_2$(py-3-COOH)(py-3-COO)], 0.1 M KCl, 16 mM Chaps and 0.1 M Tris buffer (pH9.0) recorded with a scan rate of 100 mV·s$^{-1}$.
Figure 22:
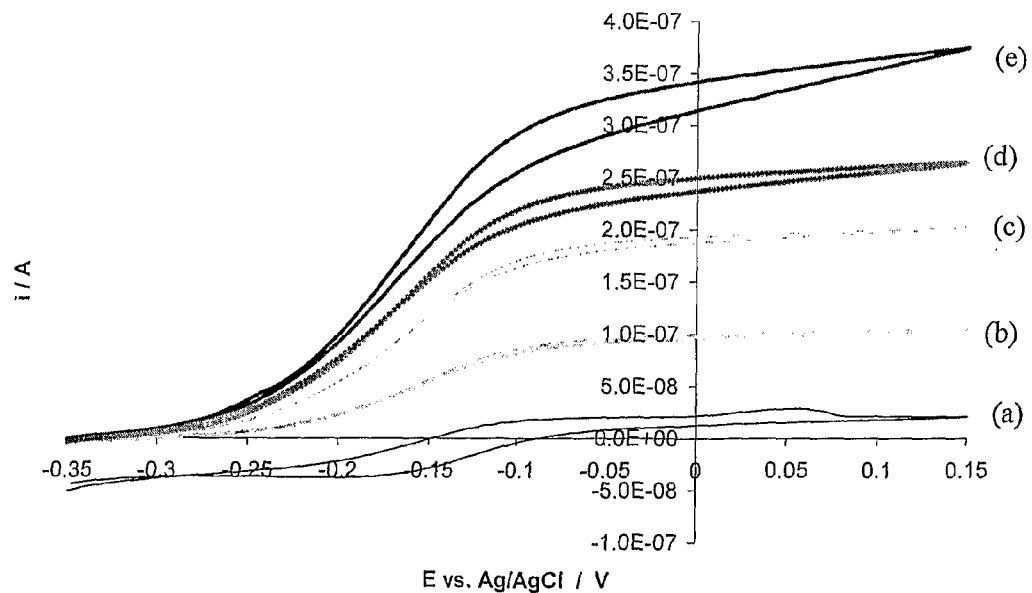
FIG. 22 shows cyclic voltammograms (at 10 mV·s$^{-1}$) of [Ru$^{III}$(5-Cl-Quin)$_2$(py-3-COOH)(py-3-COO)] (1 mM) in a 0.1 M Tris buffer (pH9.0) on a screen printed carbon microelectrode strip, containing (a) 0, (b) 0.1, (c) 0.5, (d) 1 and (e) 5 mg·ml$^{-1}$ PdR in the presence of 10 mM NADH.
Figure 23:
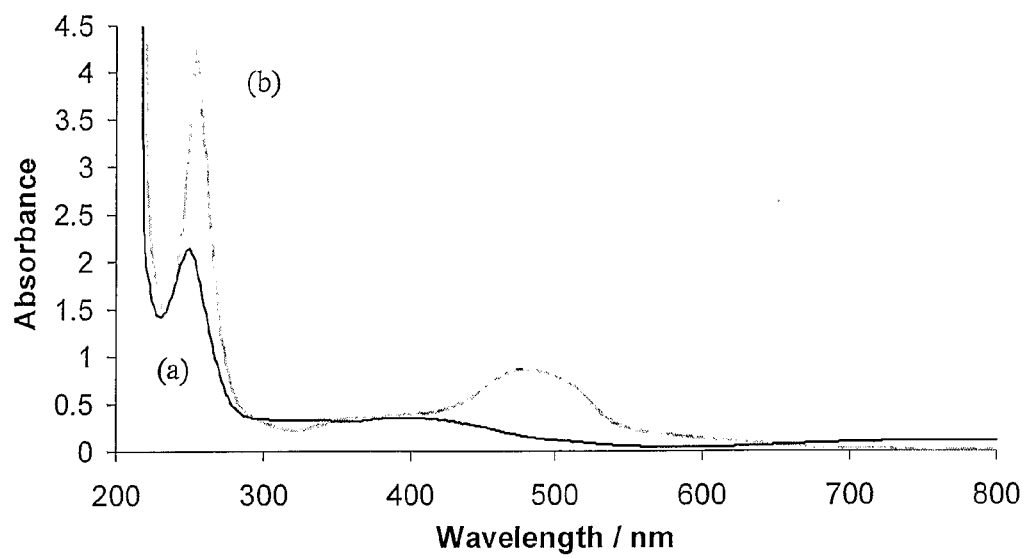
FIG. 23 shows UV-Vis absorption spectrum of a solution containing 0.25 mM [Ru$^{III}$(5-Cl-Quin)$_2$(py-3-COOH)(py-3-COO)] and 0.25 mM NADH in the absence (dark—(a)) and presence (light—(b)) of 0.033 mg·ml$^{-1}$ PdR.
Figure 24:
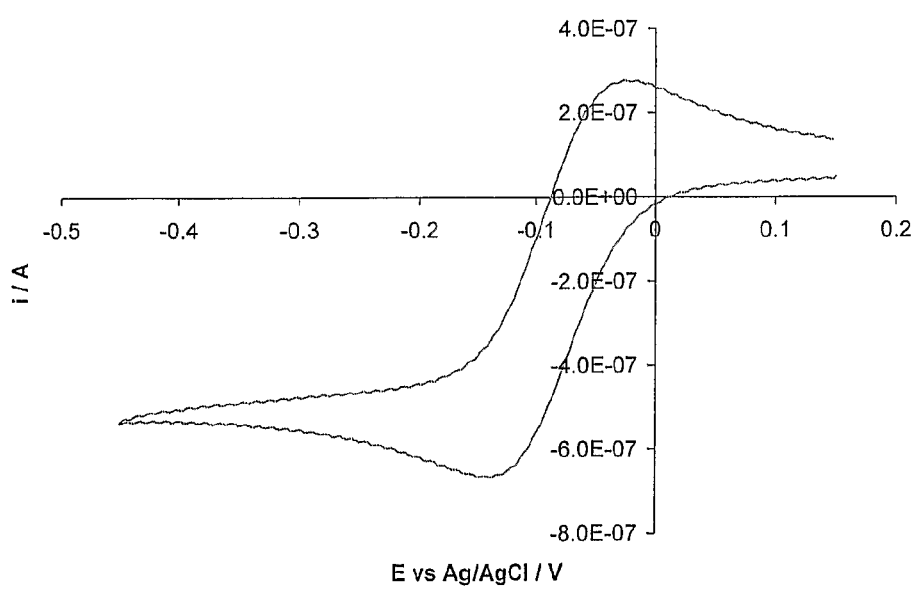
FIG. 24 shows a cyclic voltammogram for a screen printed carbon micro-electrode strip in a solution consisting of 5 mM [Ru$^{III}$(Me$_6$-tet)(acac)](PF$_6$)(CF$_3$SO$_3$), 0.1 M KCl, 16 mM Chaps and 0.1 M Tris buffer (pH9.0) recorded with a scan rate of 100 mV·s$^{-1}$.
Figure 25:
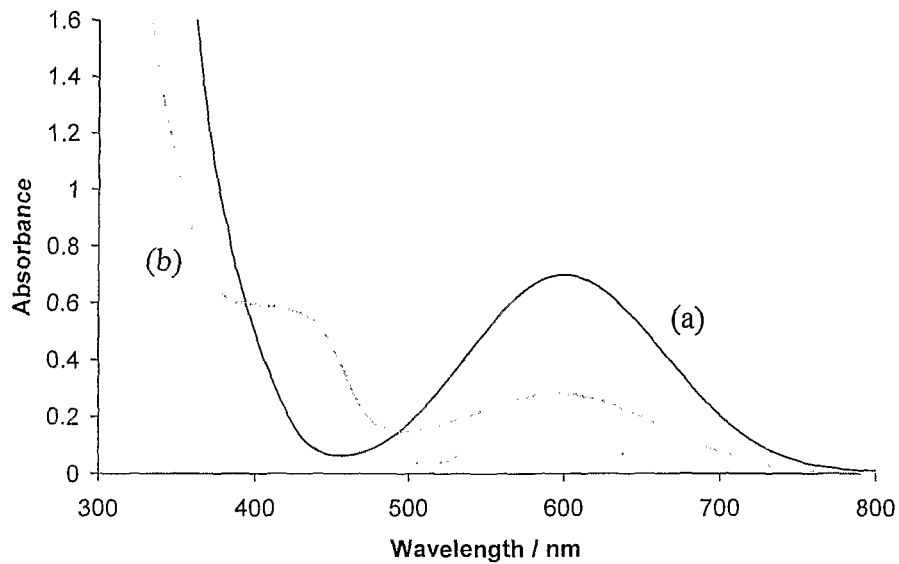
FIG. 25 shows a UV-vis absorbption spectrum of a solution consisting of 5 mM [Ru$^{III}$(Me$_6$-tet)(acac)](PF$_6$)(CF$_3$SO$_3$) and 0.5 mM NADH in the absence (dark—(a)) and presence (grey—(b)) of 0.033 mg·ml$^{-1}$ PdR.
Figure 26:
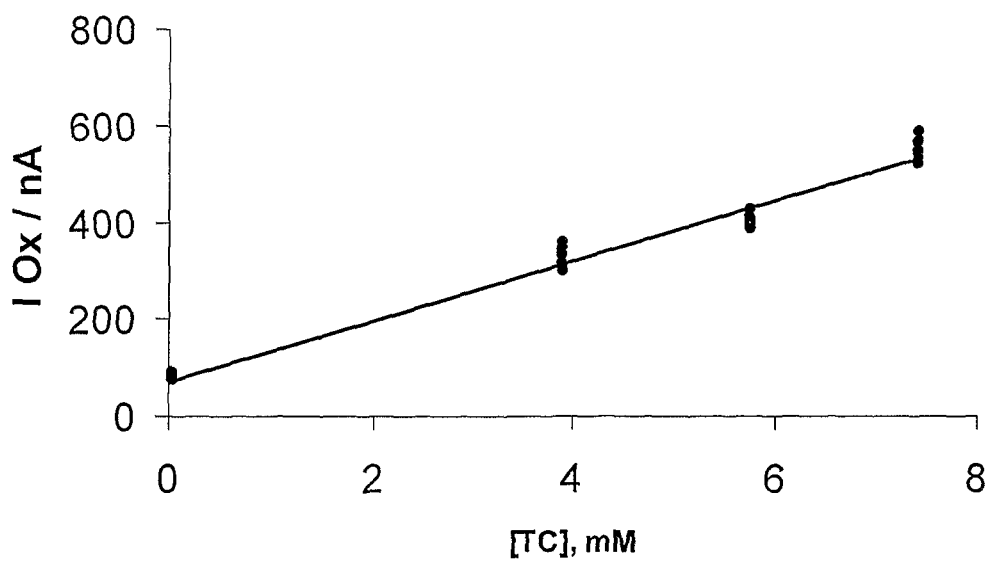
FIG. 26 shows a plot of oxidation current versus the total cholesterol (TC) concentration for different human plasma samples in wells using [Ru$^{III}$(Me$_6$-tet)(acac)](PF$_6$)(CF$_3$SO$_3$) as the mediator. Currents were recorded after an oxidation potential of +0.15 V (vs Ag/AgCl reference) was applied.
Figure 27:
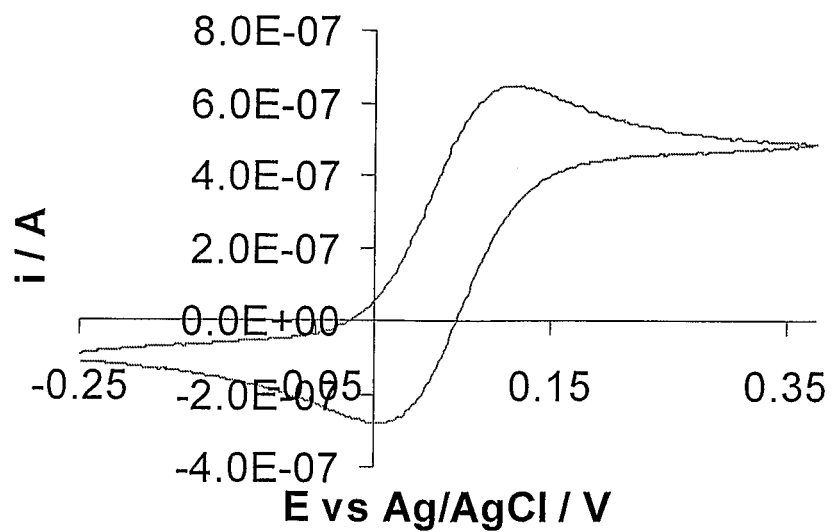
FIG. 27 shows a cyclic voltammogram for a screen printed carbon micro-electrode strip in a solution consisting of 10 mM [Os$^{II}$(2,2'-bpy)$_2$(acac)]Cl, 0.1 M KCl, 16 mM Chaps and 0.1 M Tris buffer (pH9.0) recorded with a scan rate of 100 mV·s$^{-1}$.

FIG. 9 shows the appearance of the mediator in a low oxygen atmosphere (reduced form) and in air (oxidized form). The low-oxygen solutions were prepared by first boiling water in a container, which was subsequently sealed, and then purging with N$_2$ for 20 min. The container was then sealed with parafilm and transferred to an inert atmosphere glove box (<9 ppm O$_2$). Once inside, the deoxygenated water was used to make 0.1 M KCl, which was subsequently added to the new mediator to make up a 10 mM solution. The solution appeared red (below left FIG.), while a solution made using oxygenated water (and left for 4 hours) appears yellow (right figure).

The different redox states of the mediator have different colours, which can be used for spectroscopic measurements.

The complexes of the present invention have low positive or negative charges (from +2 to −1 at pH7-10) and form less strong complexes or none at all with the components of the analytical mixture and the electrode, thus leading to more reliable, stable and reproducible electrochemical process. In addition, attention is also paid to ensure the absence of a rapid oxidation of the ruthenium(II) species by molecular oxygen.

The new mediators ensure that the enzymatic reactions are not complicated by problems connected with association of proteins, enzymes and other negatively-charged species with the electrodes. In other words, the ruthenium species are able to do efficiently the job intended for them: acting as efficient and effective electron transfer mediators. These compounds,

The invention claimed is:

1. A complex according to Formula I $$[M(A)_x(B)_y]^m(X^Z)_n \qquad \text{Formula I}$$

wherein
M is ruthenium or osmium and has an oxidation state of 0, 1, 2, 3 or 4;
x, and n are independently an integer selected from 1 to 6; y is an integer selected from 1 to 5; m is an integer from −5 to +4 and z is an integer from −2 to +1;
A is a mono- or bidentate aromatic ligand containing 1 or 2 nitrogen atoms;
B is independently selected to be one or more ligands other than a heterocyclic nitrogen-containing ligand;
X comprises a combination of $PF_6^-$ and $CF_3SO_3^-$ counterions;
wherein A is optionally substituted by 1 to 8 groups independently selected from the group consisting of substituted or unsubstituted alkyl, alkenyl, or aryl groups, —F, —Cl, —Br, —I, —$NO_2$, —CN, —$CO_2H$, —$SO_3H$, —$NHNH_2$, —SH, alkoxycarbonyl, alkylaminocarbonyl, dialkylaminocarbonyl, —OH, alkoxy, —$NH_2$, alkylamino, dialkylamino, alkanoylamino, arylcarboxamido, hydrazino, alkylhydrazino, hydroxylamino, alkoxyamino, and alkylthio;
wherein the number of coordination atoms is 6.

2. A redox mediator comprising the complex as claimed in claim 1.

3. The redox mediator as claimed in claim 2 wherein A is a monodentate ligand substituted by one or more $CO_2H$ groups, or a bidentate ligand optionally substituted by one or more $CO_2H$ groups.

4. The redox mediator as claimed in claim 2 wherein A is selected from the group consisting of nicotinic acid, isonicotinic acid, 2,2' bipyridine, 2,2-bipyridyl-5,5'-dicarboxylic acid, 2,2-bipyridyl-4,4'-dicarboxylic acid, and 5-chloro-8-hydroxyquinoline.

5. The redox mediator as claimed in claim 2 wherein B is selected from the group consisting of amine ligands, CO, CN, halogen, acetylacetonate, 3-bromoacetylacetonate, oxalate, pyridine, and 5-chloro-8-hydroxyquinoline.

6. The redox mediator as claimed in claim 2 wherein the oxidation state of the metal is selected to be 3+.

7. The redox mediator as claimed in claim 2 wherein the ligands A and B are selected such that the overall charge on the complex is selected from the group consisting of +3, +2, +1, 0, −1, −2 and −3.

8. A complex as claimed in claim 1 wherein A is a monodentate ligand substituted by one or more $CO_2H$ groups, or a bidentate ligand optionally substituted by one or more $CO_2H$ groups wherein said one or more $CO_2H$ groups are each in a meta position relative to the co-ordinating heteroatom or heteroatoms.

9. A complex as claimed in claim 1 wherein A is selected from the group consisting of nicotinic acid, isonicotinic acid, 5-carboxynicotinic acid, 6-pyridyl-nicotinic acid, 2,2'-bipyridine-5,5'-bis-carboxylic acid, 2,2'-bipyridine-4,4'-bis-carboxylic acid, 2,2'-bipyridine, and 1,10-phenanthroline-3,9-bis-carboxylic acid.

10. A complex as claimed in claim 1 wherein B is selected from the group consisting of amine ligands; CO; CN; halogen, acetylacetonate, 3-bromoacetylacetonate, oxalate, and 5-chloro-8-hydroxyquinoline.

11. A complex as claimed in claim 1 wherein the ligands A and B are selected such that the overall charge on the complex is selected from the group consisting of +2, +1, 0, −1, −2 and −3.

12. A complex as claimed in claim 1 wherein said complex is $[Ru^{III}(NH_3)_5(\text{pyridine-3-COOH})](PF_6)_2(CF_3SO_3)$.

13. The redox mediator as claimed in claim 2 wherein said complex is $[Ru^{III}(NH_3)_5(\text{pyridine-3-COOH})](PF_6)_2(CF_3SO_3)$.

14. A complex according to Formula I $$[M(A)_x(B)_y]^m(X^Z)_n \qquad \text{Formula I}$$

wherein
M is ruthenium or osmium and has an oxidation state of 0, 1, 2, 3 or 4;
x, and n are independently an integer selected from 1 to 6; y is an integer selected from 1 to 5; m is an integer from −5 to +4 and z is an integer from −2 to +1;
A is a mono- or bidentate aromatic ligand containing 1 or 2 nitrogen atoms;
B is independently selected to be one or more ligands other than a heterocyclic nitrogen-containing ligand;
X comprises a combination of two $PF_6^-$ counterions and one $CF_3SO_3^-$ counterion;
wherein A is optionally substituted by 1 to 8 groups independently selected from the group consisting of substituted or unsubstituted alkyl, alkenyl, or aryl groups, —F, —Cl, —Br, —I, —$NO_2$, —CN, —$CO_2H$, —$SO_3H$, —$NHNH_2$, —SH, alkoxycarbonyl, alkylaminocarbonyl, dialkylaminocarbonyl, —OH, alkoxy, —$NH_2$, alkylamino, dialkylamino, alkanoylamino, arylcarboxamido, hydrazino, alkylhydrazino, hydroxylamino, alkoxyamino, and alkylthio;
wherein the number of coordination atoms is 6.

* * * * *